US012703868B2

(12) United States Patent
Chilcoat et al.

(10) Patent No.: US 12,703,868 B2
(45) Date of Patent: Aug. 11, 2026

(54) METHODS AND COMPOSITIONS FOR MULTIPLEXED EDITING OF PLANT CELL GENOMES

(71) Applicant: PIONEER HI-BRED INTERNATIONAL, INC., Johnston, IA (US)

(72) Inventors: Nicholas Doane Chilcoat, Clive, IA (US); Joseph Evans, Johnston, IA (US); Yi Jia, Zionsville, IN (US); Eli Rodgers-Melnick, Johnston, IA (US); Joshua K Young, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 473 days.

(21) Appl. No.: 17/760,407

(22) PCT Filed: Feb. 3, 2021

(86) PCT No.: PCT/US2021/016353

§ 371 (c)(1),
(2) Date: Aug. 9, 2022

(87) PCT Pub. No.: WO2021/162909

PCT Pub. Date: Aug. 19, 2021

(65) Prior Publication Data

US 2023/0183724 A1 Jun. 15, 2023

Related U.S. Application Data

(60) Provisional application No. 62/972,901, filed on Feb. 11, 2020.

(51) Int. Cl.

*C12N 15/82* (2006.01)
*G06N 3/08* (2023.01)
*G16B 20/50* (2019.01)
*G16B 40/20* (2019.01)

(52) U.S. Cl.

CPC ..... *C12N 15/8213* (2013.01); *C12N 15/8241* (2013.01); *G06N 3/08* (2013.01); *G16B 20/50* (2019.02); *G16B 40/20* (2019.02); *C12N 2310/20* (2017.05)

(58) Field of Classification Search

None
See application file for complete search history.

(56) References Cited

U.S. PATENT DOCUMENTS

2011/0301854 A1 12/2011 Curry et al.
2018/0181704 A1 6/2018 Stupp
2019/0144879 A1* 5/2019 Kaeppler ........... C12N 15/8262 800/320.1
2019/0264232 A1 8/2019 Hou et al.
2021/0130800 A1 5/2021 Zhang et al.

FOREIGN PATENT DOCUMENTS

AU 2017286122 A1 11/2018
WO 2016/196489 A1 12/2016
WO 2019071048 A1 4/2019
WO 2019084062 A1 5/2019
WO 2019/217354 A1 11/2019
WO 2020/005667 A1 1/2020

OTHER PUBLICATIONS

Li et al. Genome Biology (2018)19:59.*
Zong et al. Nature Biotechnology (2017) 35(5):438.*
Kumar et al. Nature protocol (2009), vol. 4 (8): 1073-1082.*
International Preliminary Report on Patentability for International Application No. PCT/US2021/016353, mailed Aug. 25, 2022, 12 Pages.
Haeussler M., et al., "Evaluation of Off-target and On-target Scoring Algorithms and Integration into the Guide RNA Selection Tool CRISPOR," GenomeBiology, 2016, vol. 17, No. 1, pp. 1-12.
Kim J., et al., "Precision Genome Engineering Through Adenine and Cytosine Base Editing", Nature Plants, 2018, vol. 4, No. 3, pp. 148-151.
Komor A.C., et al., "Programmable Editing of a Target Base in Genomic DNA without Double-Stranded DNA Cleavage," Nature, 2016, vol. 533, No. 7603, pp. 420-424.
Mezmouk S., et al., "The Pattern and Distribution of Deleterious Mutations in Maize," G3: Genes, Genomes, Genetics, 2014, vol. 4, No. 1, pp. 163-171.
Renaut S., et al., "The Accumulation of Deleterious Mutations as a Consequence of Domestication and Improvement in Sunflowers and Other Compositae Crops," Molecular Biology and Evolution, 2015, vol. 32, No. 9, pp. 2273-2283.
Sadhu M., et al., "Highly Parallel Genome Variant Engineering with CRISPR-Cas9," Nature genetics, 2018, vol. 50, No. 4, pp. 510-514.
Supplementary European Search Report for European Application No. 21754051.7, mailed Mar. 15, 2024, 15 Pages.
International Search Report and Written Opinion for International Application No. PCT/US2021/016353, Mailed Apr. 22, 2021.

* cited by examiner

*Primary Examiner* — Medina A Ibrahim

(57) ABSTRACT

Methods and compositions are provided for massively parallel base editing in the genome of an organism, such as a plant. Multiple loci are selected based on one or more specific criteria, such as evolutionary conservation, recombination frequency, nonsense mutations, and/or missense mutations. Predictive models for deleterious alleles and biologically-informed phenotype prediction may be developed and refined based on the editing results, and improved plant lines for commercial or breeding purposes may be obtained.

44 Claims, 8 Drawing Sheets

Specification includes a Sequence Listing.

■ nonsense_freqs ▨ synonymous_freqs

Frequency 0.00
0.10
0.20
0.30
0.40
0.50
0.60
0.70

HMP Allele Frequency 0.00 0.05 0.10 0.15 0.20 0.25 0.30 0.35 0.40 0.45 0.50 0.55 0.60 0.65 0.70 0.75 0.80 0.85 0.90 0.95

Probability of successful edit 10
8
6
4
2
0

0.0 0.2 0.4 0.6 0.8 1.0

Effect of Edit

Probability of successful edit 2.0
1.5
1.0
0.5
0.0

0.0 0.2 0.4 0.6 0.8 1.0

Effect of Edit

| | | | | | | | | |
|---|---|---|---|---|---|---|---|---|
| MS26-BE-STOP1 | G | G | T | C | **C** | G | G | A |
| MS26-BE-STOP2 | T | G | A | G | C | **C** | A | G |
| MS26-BE-STOP3 | G | C | G | **C** | A | G | A | G |
| MS26-BE-STOP4 | C | T | A | **C** | A | G | C | G |
| MS26-BE-STOP5 | C | T | G | **C** | A | G | A | T |
| MS26-BE-STOP6 | G | G | C | **C** | G | A | G | A |
| MS26-BE-STOP7 | T | C | G | T | **C** | G | A | G |

METHODS AND COMPOSITIONS FOR MULTIPLEXED EDITING OF PLANT CELL GENOMES

CROSS-REFERENCE TO RELATED APPLICATIONS

This application is a 371 National Stage Entry of PCT Application No. PCT/US2021/016353, filed Feb. 3, 2021, which in turn claims the benefit of U.S. Provisional Patent Application No. 62/972,901, filed Feb. 11, 2020, all of which are incorporated by reference herein in their entireties.

FIELD OF THE INVENTION

The disclosure relates to the field of plant molecular biology, in particular, to compositions and methods for altering the genome of a cell.

REFERENCE TO SEQUENCE LISTING SUBMITTED ELECTRONICALLY

The official copy of the sequence listing is submitted electronically via EFS-Web as an ASCII formatted sequence listing with a file named 8051-WO-PCT_SequenceListing_ST25.txt created on 1 Feb. 2021 and having a size of 27,611 bytes and is filed concurrently with the specification. The sequence listing contained in this ASCII formatted document is part of the specification and is herein incorporated by reference in its entirety.

BACKGROUND

Every genome contains some number of deleterious mutations, or alleles that when optimized would provide greater fitness to the organism, which together comprise the genetic load. Within the field of plant breeding, selection is traditionally used to improve the desired agronomic phenotypes and thereby gradually purge the genetic load of the breeding population. Agronomic phenotypes such as yield generally have complex genetic architectures, lacking any major single-gene candidates for genome editing. While strong, dominant deleterious variants may be quickly eliminated during the breeding process, slightly deleterious mutations or those with incompletely dominant effects may persist in the breeding population for long periods of time. Moreover, large regions of suppressed recombination within many crop genomes effectively halt purging of individual deleterious variants.

Gene editing provides one potential means of removing deleterious variation independently or in combination with breeding efforts. However, the production of double-strand breaks combined with the semi-stochastic nature of DNA repair limits the feasibility of highly-parallel editing, which is a necessary feature for making a significant impact on complex traits when the individual effects are expected to be small. Because of these and other factors, there remains a need in the field of plant breeding a need for rapid elimination of potentially deleterious alleles in order to create more robust plants.

SUMMARY OF INVENTION

Provided herein are methods and compositions for massively parallel base editing of genomes, such as plant genomes, to produce an organism with improved or desired characteristics.

In some aspects, methods and compositions provided for the identification of candidate alleles and/or specific target sites in a genome for editing.

In some aspects, a guide polynucleotide is provided to the organism, for example a plant or a plant cell, with an inactivated Cas endonuclease, wherein the guide polynucleotide and the Cas endonuclease form a complex that recognizes and binds to one or more target site(s) in the genome of the organism. In some embodiments, the guide polynucleotide and the Cas endonuclease are introduced into the organism with a deaminase, that is capable of deaminating a nucleotide in the target site, to convert it from one kind of nucleobase to another, for example a Cytosine to a Uracil. In some aspects, an additional molecule (e.g., a uracil glycosylase inhibitor) is also introduced to prevent the reversion of a Uracil back to a Cytosine, such that the cellular DNA repair mechanisms allow the base pair to become A-T in place of the original G-C. In another example, the deaminase is an adenosine deaminase, that converts an Adenine to a Guanine. The guide polynucleotide, the Cas endonuclease, the deaminase, and/or any other heterologous molecule provided to the target site may be introduced individually or as part of a complex; and/or introduced simultaneously or sequentially; and/or introduced as polypeptides or as polynucleotides encoding polypeptides.

In some aspects, methods and compositions are provided for the design and introduction to a genome of a plurality of guide polynucleotides, each of which shares some percent identity with a target site in the genome.

In some aspects, methods and compositions are provided for editing a plurality of target sites in the genome of an organism, such as a plant. In some embodiments, a plurality includes 2, 3, 4, 5, 6, 7, 8 9, 10, or greater than 10, greater than 20, greater than 30, greater than 40, greater than 50, greater than 60, greater than 70, greater than 80, greater than 90, greater than 100, greater than 200, greater than 300, greater than 400, greater than 500, greater than 600, greater than 700, greater than 800, greater than 900, or greater than 1000 target sites.

In some aspects, methods and compositions are provided for evaluating an organism that has had a plurality of target sites in its genome modified via the use of a plurality of guide polynucleotides.

In some aspects, methods and compositions are provided for the assessment or evaluation of the phenotype of the edited organism.

In some aspects, methods and compositions are provided for the use of the edited organism for the production of progeny lines that comprise the edits.

In some aspects, methods and compositions are provided for the production of one or more such edited organisms, and subsequent sexual reproduction of the edited organism(s) in a breeding program.

In some aspects, methods and compositions are provided for the creation and optimization of a predictive algorithm for multiplexed plant editing.

In some aspects, a method is provided for identifying a plurality of loci in the genome of a plant for modification, comprising: calculating selection scores of a plurality of target sites in the plant genome; identifying a plurality of target sites of (a) with selection scores that match one or more user-defined criterion/a, and selecting target sites of (b) that each comprise a sequence that is capable of being recognized by an RNA-guided protein. In some embodiments of this aspect, the selection score is based on evolutionary conservation of the target site. In some embodiments of this aspect, the selection score is based on a computational predictive model. In some embodiments of this aspect, the selection score is based on biochemical or biophysical properties of the target site. In some embodiments of this aspect, the selection score is based on a plurality of scores. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for selecting a plurality of target sites for desired nucleobase editing in a genome, the method comprising: calculating selection scores of a plurality of target sites in the plant genome; selecting target sites of (a) with selection scores that match one or more user-defined criterion/a; selecting target sites of (b) that each comprise a sequence that is capable of being recognized by an RNA-guided protein; and selecting target sites of (c) that comprise the desired nucleobase. In some embodiments of this aspect, the selection score is based on evolutionary conservation of the target site. In some embodiments of this aspect, the selection score is based on a computational predictive model. In some embodiments of this aspect, the selection score is based on biochemical or biophysical properties of the target site. In some embodiments of this aspect, the selection score is based on a plurality of scores. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for creating a plurality of edits in the genome of a plant, the method comprising: selecting a plurality of target sites that each comprise a desired nucleobase; introducing into at least one cell of the plant: a plurality of different guide RNAs that each share sufficient homology with at least one of the plurality of target sites in the genome, a plurality of proteins that each forms a complex with a guide RNA, a base editing agent; wherein the base editing agent chemically alters the desired nucleobase at at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, or greater than 95% of the plurality of target sites. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for altering a characteristic of a plant, the method comprising: selecting a plurality of target sites that each comprise a desired nucleobase; introducing into at least one cell of the plant a composition comprising: a plurality of different guide RNAs that each share sufficient homology with at least one of the plurality of target sites in the genome, a plurality of proteins that each forms a complex with a guide RNA, and a base editing agent; obtaining or deriving a whole plant from the cell of the plant, assessing the plant for the presence of at least one altered characteristic, as compared to an isoline plant that did not have the composition of (b) introduced into it; wherein the base editing agent chemically alters the desired nucleobase at at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, or greater than 95% of the plurality of target sites. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for altering a characteristic of a plant, the method comprising: selecting a plurality of target sites that each comprise a desired nucleobase; introducing into at least one cell of the plant a composition comprising: a plurality of different guide RNAs that each share sufficient homology with at least one of the plurality of target sites in the genome, a plurality of proteins that each forms a complex with a guide RNA, and a base editing agent; obtaining or deriving a whole plant from the cell of the plant, assessing the plant for the presence of at least one altered characteristic, as compared to an isoline plant that did not have the composition of (b) introduced into it; wherein the base editing agent chemically alters the desired nucleobase at at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, or greater than 95% of the plurality of target sites; the method further comprising crossing the plant of (c) with a second plant to obtain a third plant. In some embodiments of this aspect, the second plant is the plant of (c) and the cross is a self. In some embodiments of this aspect, the second plant is a wild type plant. In some embodiments of this aspect, the second plant is a sibling plant. In some embodiments of this aspect, the second plant is another plant comprising a plurality of edited nucleobases. In some embodiments of this aspect, the third plant is crossed with a fourth plant. In some embodiments of this aspect, wherein the third plant is the plant of (c). In some embodiments of this aspect, the third plant is a wild type plant. In some embodiments of this aspect, the third plant is a sibling plant. In some embodiments of this aspect, the third plant is another plant comprising a plurality of edited nucleobases. In some embodiments of this aspect, the third plant is a parental plant. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for of introducing genomic edits into a population of plants, the method comprising: selecting a plurality of target sites that each comprise a desired nucleobase; introducing into at least one cell of the plant a composition comprising: a plurality of different guide RNAs that each share sufficient homology with at least one of the plurality of target sites in the genome, a plurality of proteins that each forms a complex with a guide RNA, and a base editing agent; obtaining or deriving a whole plant from the cell of the plant, assessing the plant for the presence of at least one altered characteristic, as compared to an isoline plant that did not have the composition of (b) introduced into it; and crossing the plant with a second plant to obtain a population of plants; wherein the base editing agent chemically alters the desired nucleobase at at least 5%, between 5% and 10%, at least 10%, between 10% and 15%, at least 15%, between 15% and 20%, at least 20%, between 20% and 25%, at least 25%, between 25% and 30%, at least 30%, between 30% and 35%, at least 35%, between 35% and 40%, at least 40%, between 40% and 45%, at least 45%, between 45% and 50%, at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, or greater than 95% of the plurality of target sites. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for predicting the outcome of allele modification in plants, the method comprising: selecting a plurality of loci for potential nucleobase editing, choosing a model distribution for the effects of the edits, choosing a model distribution for the probability of success of the edits, simulating the measured phenotype for a variable number of plants, assessing the effects of the edits, and estimating the allele effects. In some embodiments of this aspect, the effects of the edits of (e) are additive. In some embodiments of this aspect, the effects of the edits of (e) are multiplicative. In some embodiments of this aspect, the effects of the edits include a noise factor, optionally a Gaussian factor or a non-Gaussian factor. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for improving the prediction of the outcome of allele modification in plants, the method comprising: selecting a plurality of loci for potential nucleobase editing, choosing a model distribution for the effects of the edits, choosing a model distribution for the probability of success of the edits, simulating the measured phenotype for a variable number of plants, assessing the effects of the edits, and estimating the allele effects; the method further comprising adjusting the model distribution of (b) or the model distribution of (c) with information obtained from in vivo experimental data. In some embodiments of this aspect, the effects of the edits of (e) are additive. In some embodiments of this aspect, the effects of the edits of (e) are multiplicative. In some embodiments of this aspect, the effects of the edits include a noise factor, optionally a Gaussian factor or a non-Gaussian factor. In some embodiments of this aspect, the plurality of target sites or plurality of loci is at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500. In some embodiments of this aspect, the plurality of different guide RNAs comprise single guide RNAs. In some embodiments of this aspect, wherein the plurality of different guide RNAs are formed from a common tracrRNA and a plurality of different crRNAs. In some embodiments of this aspect, the guide RNAs are introduced by particle bombardment. In some embodiments of this aspect, the guide RNAs are introduced by *Agrobacterium*-mediated transformation. In some embodiments of this aspect, the guide RNAs are introduced via a plurality of different *Agrobacterium* strains. In some embodiments of this aspect, the guide RNAs are each part of a different heterologous polynucleotide. In some embodiments of this aspect, some of the guide RNAs are present on a common heterologous polynucleotide. In some embodiments of this aspect, a plurality of variable targeting domains are provided on a contiguous polynucleotide. In some embodiments of this aspect, the RNA-guided proteins are not identical. In some embodiments of this aspect, the RNA-guided protein is a Cas endonuclease. In some embodiments of this aspect, the RNA-guided protein is a Cas9 endonuclease. In some embodiments of this aspect, the desired nucleobase is Cytosine. In some embodiments of this aspect, the desired nucleobase is Adenine.

In some aspects, a method is provided for parallel editing of a plurality of unrelated genomic single nucleotide polymorphisms (SNPs) in a plant genome, the method comprising: selecting the plurality of SNPs based on a scoring matrix derived from screening polymorphic sites using a combination of a SNP dataset and/or a high-density genome-wide haplotype map or a local haplotype map targeted to a specific chromosome or a segment of the chromosome, wherein the plurality of SNPs comprises at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500 or more unlinked genetic loci; identifying SNPs that are predicted to occur within annotated coding sequences of one or more plant genes in the plant genome; assigning a probability score for sorting intolerant from tolerant (SIFT) for the plurality of SNPs based on whether a proposed base substitution is likely to be tolerated or selected against based on protein function and/or amino acid conservation; and selecting the plurality of SNPs for editing based on the SIFT score, wherein the selected SNPs are capable of being edited through a C→T base editing or an A>G base editing.

In some aspects, a method is provided for parallel editing of a plurality of unrelated genomic single nucleotide polymorphisms (SNPs) in a plant genome, the method comprising: selecting the plurality of SNPs based on a scoring matrix derived from screening polymorphic sites using a combination of a SNP dataset and/or a high-density genome-wide haplotype map or a local haplotype map targeted to a specific chromosome or a segment of the chromosome, wherein the plurality of SNPs comprises at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500 or more unlinked genetic loci; identifying SNPs that are predicted to occur within annotated coding sequences of one or more plant genes in the plant genome; assigning a probability score for sorting intolerant from tolerant (SIFT) for the plurality of SNPs based on whether a proposed base substitution is likely to be tolerated or selected against based on protein function and/or amino acid conservation; and selecting the plurality of SNPs for editing based on the SIFT score, wherein the selected SNPs are capable of being edited through a C→T base editing or an A>G base editing; wherein the plurality of SNPs selected include C and G alleles in the plant genome with a SIFT score of about 0.075 or lower that correspond to segregating T and A alleles, respectively, with a SIFT score of about 0.4 or higher.

In some aspects, a method is provided for parallel editing of a plurality of unrelated genomic single nucleotide polymorphisms (SNPs) in a plant genome, the method comprising: selecting the plurality of SNPs based on a scoring matrix derived from screening polymorphic sites using a combination of a SNP dataset and/or a high-density genome-wide haplotype map or a local haplotype map targeted to a specific chromosome or a segment of the chromosome, wherein the plurality of SNPs comprises at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500 or more unlinked genetic loci; identifying SNPs that are predicted to occur within annotated coding sequences of one or more plant genes in the plant genome; assigning a probability score for sorting intolerant from tolerant (SIFT) for the plurality of SNPs based on whether a proposed base substitution is likely to be tolerated or selected against based on protein function and/or amino acid conservation; and selecting the plurality of SNPs for editing based on the SIFT score, wherein the selected SNPs are capable of being edited through a C→T base editing or an A>G base editing; wherein plurality of SNPs selected are enriched for their deleterious effects.

In some aspects, a method is provided for parallel editing of a plurality of unrelated genomic single nucleotide polymorphisms (SNPs) in a plant genome, the method comprising: selecting the plurality of SNPs based on a scoring matrix derived from screening polymorphic sites using a combination of a SNP dataset and/or a high-density genome-wide haplotype map or a local haplotype map targeted to a specific chromosome or a segment of the chromosome, wherein the plurality of SNPs comprises at least 2, between 2 and 5, at least 5, between 5 and 10, at least 10, between 10 and 50, at least 50, between 50 and 100, at least 100, between 100 and 200, at least 200, between 200 and 300, at least 300, at least 300, between 300 and 400, at least 400, between 400 and 500, at least 500, or greater than 500 or more unlinked genetic loci; identifying SNPs that are predicted to occur within annotated coding sequences of one or more plant genes in the plant genome; assigning a probability score for sorting intolerant from tolerant (SIFT) for the plurality of SNPs based on whether a proposed base substitution is likely to be tolerated or selected against based on protein function and/or amino acid conservation; and selecting the plurality of SNPs for editing based on the SIFT score, wherein the selected SNPs are capable of being edited through a C→T base editing or an A>G base editing; wherein the scoring matrix provides a higher score for rarer alleles.

In some aspects, the deaminase is selected from the group consisting of: SEQID NOs: 1-16. In some aspects, the promoter is selected from the group consisting of: SEQID NOs:17-22.

BRIEF DESCRIPTION OF THE DRAWINGS

The disclosure can be more fully understood from the following detailed description and the accompanying drawings and Sequence Listing, which form a part of this application.

Figure 1:
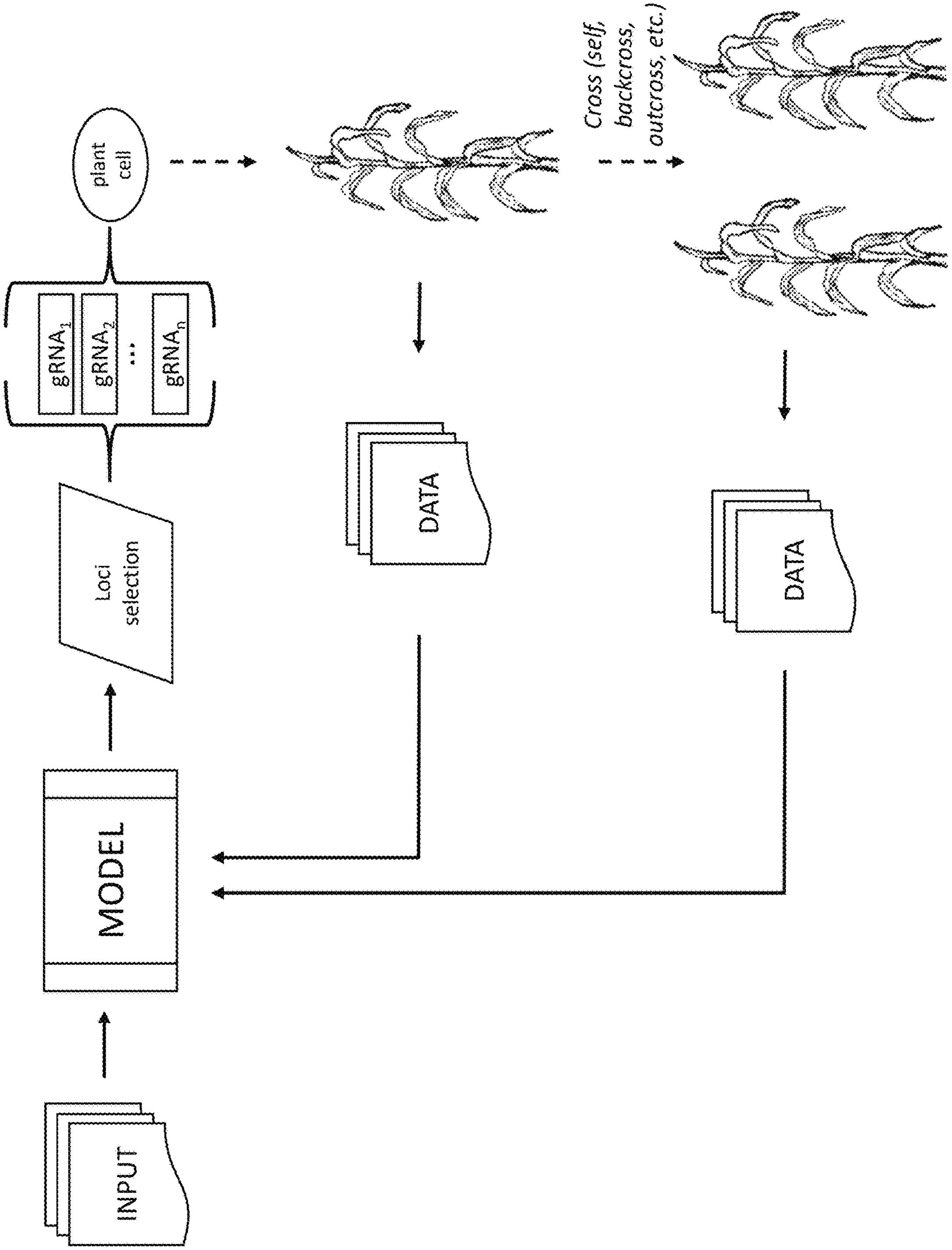
FIG. 1 depicts the schema for creating and refining a model algorithm for multiple allele selection in an organism, for example a plant, for identification of loci for base editing.

The sequence descriptions and sequence listing attached hereto comply with the rules governing nucleotide and amino acid sequence disclosures in patent applications as set forth in 37 C.F.R. §§ 1.821 1.825. The sequence descriptions contain the three letter codes for amino acids as defined in 37 C.F.R. §§ 1.821 1.825, which are incorporated herein by reference.

SEQID NO:1 is the *E. coli* tRNA adenine deaminase PRT sequence from *Escherichia coli.*

SEQID NO:2 is the Novel deaminase 1 PRT sequence from Enterobacteriaceae bacterium strain FGI 57.

SEQID NO:3 is the Novel deaminase 2 PRT sequence from *Kluyvera georgiana.*

SEQID NO:4 is the Novel deaminase 3 PRT sequence from *Klebsiella pneumoniae* (30).

SEQID NO:5 is the Novel deaminase 4 PRT sequence from *Klebsiella aerogenes* (27).

SEQID NO:6 is the Novel deaminase 5 PRT sequence from *Kluyvera ascorbata* ATCC 33433.

SEQID NO:7 is the Novel deaminase 6 PRT sequence from *Raoultella* sp. (18).

SEQID NO:8 is the Novel deaminase 7 PRT sequence from *Klebsiella* sp. RIT-PI-d.

SEQID NO:9 is the Novel deaminase 8 PRT sequence from *Pseudocitrobacter faecalis.*

SEQID NO:10 is the Novel deaminase 9 PRT sequence from *Enterobacter cloacae* (15).

SEQID NO:11 is the Novel deaminase 10 PRT sequence from *Citrobacter youngae.*

SEQID NO:12 is the Novel deaminase 11 PRT sequence from *Kosakonia pseudosacchari.*

SEQID NO:13 is the Novel deaminase 12 PRT sequence from *Pluralibacter gergoviae.*

SEQID NO:14 is the Novel deaminase 13 PRT sequence from *Klebsiella pneumoniae.*

SEQID NO:15 is the Novel deaminase 14 PRT sequence from *Superficieibacter electus.*

SEQID NO:16 is the Novel deaminase 15 PRT sequence from *Cronobacter malonaticus.*

SEQID NO:17 is the U6 promoter 1 DNA sequence from *Zea mays.*

SEQID NO:18 is the U6 promoter 2 DNA sequence from *Zea mays.*

SEQID NO:19 is the U6 promoter 3 DNA sequence from *Zea mays.*

SEQID NO:20 is the U6 promoter 4 DNA sequence from *Zea mays.*

SEQID NO:21 is the U6 promoter 5 DNA sequence from *Zea mays.*

SEQID NO:22 is the U6 promoter 6 DNA sequence from *Zea mays.*

SEQID NO:23 is the artificial single guide RNA 1 RNA sequence.

SEQID NO:24 is the artificial single guide RNA 2 RNA sequence.

SEQID NO:25 is the artificial single guide RNA 3 RNA sequence.

SEQID NO:26 is the artificial single guide RNA 4 RNA sequence.

DETAILED DESCRIPTION

Base editing is an alternative to editing with homologous recombination. In some aspects, a "dead" or "deactivated" Cas protein (dCas), that has been modified to lack the capability for creating either a single- or double-strand break in a target polynucleotide, or nickase Cas protein (nCas) that has been modified to lack the capability for creating a double-strand break in a target double-stranded polynucleotide but retains the capability for cleaving or nicking one strand of a double-stranded polynucleotide, is coupled to a deaminase to facilitate a base transition within a target window, without any accompanying double-strand break. Any deaminase may be used, for example a cytosine deaminase or an adenosine deaminase. In some embodiments, a cytosine deaminase is coupled to a dCas, for example a dCas9, for highly-multiplexed base editing of candidate deleterious single-nucleotide alleles within a maize inbred line. This process provides a blueprint for continuous improvement of germplasm across the genome, regardless of the power to conduct traditional selection in any genomic region.

As disclosed herein, parallel or multiplexed editing of multiple bases in the plant genome can result in significant phenotypic variation (as compared to the effect of a single edit), and there was a positive directional bias to the effects. Irrespective of individual phenotypic effects of each individual site, the cumulative fitness association impacted yield components.

Deleterious alleles can accumulate in low recombination frequency regions, rending it difficult to produce optimized germplasm, as low recombination reduces selection efficiency. Eliminating individual deleterious alleles or nucleotides is made difficult and time consuming through conventional breeding by associations, or linkage disequilibrium, between positive and negative functional sites. A genomic editing approach may be used to obviate the difficulties associated with conventional breeding. However, the effect of each individual change is small; therefore, multiplexing, particularly at a large scale (e.g., at 5, 10, 100, or even 1000 sites), is desirable. Combining edits of deleterious variants with trait selection can increase genetic gain even if the edited variants are independent of the trait of interest. Positive editing with genomic selection can be combined for increased genetic gain.

Base editing technology provides an unprecedented opportunity to remediate deleterious alleles. In some aspects, target sites are selected based on certain criteria, such as the degree of evolutionary conservation, or other selectable criterion, of a particular locus as compared to the nucleotide composition in other genomes of related organisms. The approach depends on the identification of deleterious variants within the inbred line to be edited. Putative deleterious alleles (based on evolutionary conservation) are most predictive of fitness-related traits.

Herein is described bioinformatic approaches grounded in evolutionary theory to identify candidate polymorphisms that 1) putatively contained the deleterious allele within the inbred line of interest and 2) were amenable to replacement of the deleterious allele with the non-deleterious allele using base editing.

Identification of undesirable or non-preferred bases (alleles) used bioinformatic enrichment for putative deleterious variants. Nonsense mutations and missense mutations at conserved sites were identified. To avoid the creation of undesirable or non-preferred alleles, rare alleles were prioritized and guide-dependent off-target effects were avoided.

We began with the identification of putative high-impact variants in the genome, for example, missense variants at evolutionarily conserved positions. These mutations were further ranked based on the frequency of the putative deleterious allele within maize genetic diversity datasets. The final candidate list was determined after filtering sites with the appropriate substitution configuration (C→T or G→A in the case of a cytosine deaminase), appropriate placement of the PAM, avoidance of editing neighboring sites to the position of interest, and sufficient uniqueness to avoid substantial off-target edits. The success of line improvement from this project was assessed following the recovery of edited lines by comparing reproductive traits (e.g., yield, seed weight, tassel size) in selfs of the wild type versus the edited lines. Complementation patterns were also interrogated through testcrosses with the complementary heterotic group of the edited inbred. Successful editing of true deleterious variants resulted in both increased genetic variance of independent recoveries compared to the wild type, alongside increased reproductive output. By allowing segregation of realized edits and assessing genotypes with a low-cost genotyping panel, estimates of the individual edit effects were obtained. These estimates were used to inform the subsequent selection of target sites and the introduction of edits into additional germplasm. Using previously-obtained knowledge of haplotype sharing across proprietary germplasm datasets, characterized edits may be propagated across many inbreds synergistically with classical breeding efforts.

In some aspects, genome-wide neutralization of deleterious alleles through the introduction of pre-mature stop codon is enabled by multiplexing base editing. Application of the base editing enabled STOP codon introduction technology results in partial or complete neutralization of the effects of deleterious alleles in genome wide or multiple biochemistry pathways. The loci for STOP codon introduction can be targeted in genome wide for complex trait improvement (e.g. yield) or genes from single or multiple biochemistry pathways for favorable output traits (e.g. Loss of functions of FAD genes for healthy oils in soybeans) or disease resistance traits (e.g. loss of functions of S genes for disease resistance in crops). Currently a list of potential deleterious alleles has been identified in a maize genome. And an exemplary process to identify base positions for premature STOP codon introduction in a maize gene has been demonstrated.

Although maize was used as a model, it will be understood by those of skill in the art that the methods and compositions described herein can be applied to any organism, particularly any plant, such as a monocot plant or a dicot plant.

Terms used in the claims and specification are defined as set forth below unless otherwise specified. It must be noted that, as used in the specification and the appended claims, the singular forms "a," "an" and "the" include plural referents unless the context clearly dictates otherwise.

As used herein, "nucleic acid" generally means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

A "deaminase" is an enzyme that catalyzes a deamination reaction. For example, deamination of adenine with an adenine deaminase results in the formation of hypoxanthine. Hypoxanthine selectively base pairs with cytosine instead of thymine. This results in a post-replicative transition mutation, such that the original A-T base pair transforms into a G-C base pair. In another example, cytosine deamination results in the formation of uracil, which would normally be repaired by cellular repair mechanisms back to cytosine but can be prevented introduction of a uracil glycosylase inhibitor, such that DNA repair or replication transforms the original G-C base pair into an A-T base pair.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

"Open reading frame" is abbreviated ORF.

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have structural similarity such that they are capable of acting as substrates for a homologous recombination reaction. The structural similarity includes overall length of each polynucleotide fragment, as well as the sequence similarity of the polynucleotides.

Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

As used herein, "homologous recombination" (HR) includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any percentage from 50% to 100%. These identities can be determined using any of the programs described herein.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment. Substantially similar nucleic acid sequences encompassed may be defined by their ability to hybridize (under moderately stringent conditions, e.g., 0.5X SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

A "centimorgan" (cM) or "map unit" is the distance between two polynucleotide sequences, linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Generally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. Isolated polynucleotides may be purified from a cell in which they naturally occur. Conventional nucleic acid purification methods known to skilled artisans may be used to obtain isolated polynucleotides. The term also embraces recombinant polynucleotides and chemically synthesized polynucleotides.

The term "fragment" refers to a contiguous set of nucleotides or amino acids. In one embodiment, a fragment is 2, 3, 4, 5, 6, 7 8, 9, 10, 11, 12, 13, 14, 15, 16, 17, 18, 19, 20, or greater than 20 contiguous nucleotides. In one embodiment, a fragment is 2, 3, 4, 5, 6, 7 8, 9, 10, 11, 12, 13, 14, 15, 16, 17, 18, 19, 20, or greater than 20 contiguous amino acids. A fragment may or may not exhibit the function of a sequence sharing some percent identity over the length of said fragment.

The terms "fragment that is functionally equivalent" and "functionally equivalent fragment" are used interchangeably herein. These terms refer to a portion or subsequence of an isolated nucleic acid fragment or polypeptide that displays the same activity or function as the longer sequence from which it derives. In one example, the fragment retains the ability to alter gene expression or produce a certain phenotype whether or not the fragment encodes an active protein.

For example, the fragment can be used in the design of genes to produce the desired phenotype in a modified plant. Genes can be designed for use in suppression by linking a nucleic acid fragment, whether or not it encodes an active enzyme, in the sense or antisense orientation relative to a plant promoter sequence.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in its natural endogenous location with its own regulatory sequences.

By the term "endogenous" it is meant a sequence or other molecule that naturally occurs in a cell or organism. In one aspect, an endogenous polynucleotide is normally found in the genome of a cell; that is, not heterologous.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a gene (referred to as the target gene), including a native gene, that was made by altering a target sequence within the target gene using any method known to one skilled in the art, including a method involving a guided Cas endonuclease system as disclosed herein.

The terms "knock-out", "gene knock-out" and "genetic knock-out" are used interchangeably herein. A knock-out represents a DNA sequence of a cell that has been rendered partially or completely inoperative by targeting with a Cas protein; for example, a DNA sequence prior to knock-out could have encoded an amino acid sequence, or could have had a regulatory function (e.g., promoter).

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

By "domain" it is meant a contiguous stretch of nucleotides (that can be RNA, DNA, and/or RNA-DNA-combination sequence) or amino acids.

The term "conserved domain" or "motif" means a set of polynucleotides or amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

A "codon-modified gene" or "codon-preferred gene" or "codon-optimized gene" is a gene having its frequency of codon usage designed to mimic the frequency of preferred codon usage of the host cell.

An "optimized" polynucleotide is a sequence that has been optimized for improved expression in a particular heterologous host cell.

An "optimized nucleotide sequence" is a nucleotide sequence that has been optimized for expression in a particular organism. A plant-optimized nucleotide sequence includes a codon-optimized gene. A plant-optimized nucleotide sequence can be synthesized by modifying a nucleotide sequence encoding a protein such as, for example, a Cas endonuclease as disclosed herein, using one or more plant-preferred codons for improved expression. See, for example, Campbell and Gowri (1990) *Plant Physiol.* 92:1-11 for a discussion of host-preferred codon usage.

A "promoter" is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

Promoters that cause a gene to be expressed in most cell types at most times are commonly referred to as "constitutive promoters". The term "inducible promoter" refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase.

The term "genome" refers to the entire complement of genetic material (genes and non-coding sequences) that is present in each cell of an organism, or virus or organelle; and/or a complete set of chromosomes inherited as a (haploid) unit from one parent.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Generally, "host" refers to an organism or cell into which a heterologous component (polynucleotide, polypeptide, other molecule, cell) has been introduced. As used herein, a "host cell" refers to an in vivo or in vitro eukaryotic cell, prokaryotic cell (e.g., bacterial or archaeal cell), or cell from a multicellular organism (e.g., a cell line) cultured as a unicellular entity, into which a heterologous polynucleotide or polypeptide has been introduced. In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector comprising a gene and having elements in addition to the gene that facilitates transformation of a particular host cell. "Expression cassette" refers to a specific vector comprising a gene and having elements in addition to the gene that allow for expression of that gene in a host. In one aspect, a "Donor DNA cassette" comprises a heterologous polynucleotide to be inserted at the double-strand break site created by a double-strand-break inducing agent (e.g. a Cas endonuclease and guide RNA complex), that is operably linked to a noncoding expression regulatory element. In some aspects, the Donor DNA cassette further comprises polynucleotide sequences that are homologous to the target site, that flank the polynucleotide of interest operably linked to a noncoding expression regulatory element.

The terms "recombinant DNA molecule", "recombinant DNA construct", "expression construct", "construct", and "recombinant construct" are used interchangeably herein. A recombinant DNA construct comprises an artificial combination of nucleic acid sequences, e.g., regulatory and coding sequences that are not all found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to introduce the vector into the host cells as is well known to those skilled in the art.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from *Zea mays* would be heterologous if inserted into the genome of an *Oryza sativa* plant, or of a different variety or cultivar of *Zea mays*; or a polynucleotide obtained from a bacterium was introduced into a cell of a plant), or sequence (e.g., a polynucleotide sequence obtained from *Zea mays*, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, one or more regulatory region (s) and/or a polynucleotide provided herein may be entirely synthetic. In one aspect, a discrete component of a poly-gRNA molecule is heterologous to at least one other component, i.e., do not occur together in nature.

The term "expression", as used herein, refers to the production of a functional end-product (e.g., an mRNA, guide RNA, or a protein) in either precursor or mature form.

A "mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, Science 327:167-170; WO2007025097, published 1 Mar. 2007). A CRISPR locus can include of a CRISPR array, comprising short direct repeats (CRISPR repeats) separated by short variable DNA sequences (called spacers), which can be flanked by diverse Cas (CRISPR-associated) genes.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes but is not limited to: a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence. A Cas endonuclease described herein comprises one or more nuclease domains. The endonucleases of the disclosure may include those having one or more RuvC nuclease domains. A Cas protein is further defined as a functional fragment or functional variant of a native Cas protein, or a protein that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native Cas protein, and retains at least partial activity.

A "Cas endonuclease" may comprise domains that enable it to function as a double-strand-break-inducing agent. A "Cas endonuclease" may also comprise one or more modifications or mutations that abolish or reduce its ability to cleave a double-strand polynucleotide (dCas). In some aspects, the Cas endonuclease molecule may retain the ability to nick a single-strand polynucleotide (for example, a D10A mutation in a Cas9 endonuclease molecule) (nCas9).

A "functional fragment", "fragment that is functionally equivalent" and "functionally equivalent fragment" of a Cas endonuclease are used interchangeably herein, and refer to a portion or subsequence of the Cas endonuclease of the present disclosure in which the ability to recognize, bind to, and optionally unwind, nick or cleave (introduce a single or double-strand break in) the target site is retained. The portion or subsequence of the Cas endonuclease can comprise a complete or partial (functional) peptide of any one of its domains such as for example, but not limiting to a complete of functional part of a Cas3 HD domain, a complete of functional part of a Cas3 Helicase domain, complete of functional part of a Cascade protein (such as but not limiting to a Cas5, Cas5d, Cas7 and Cas8b1).

The terms "functional variant", "variant that is functionally equivalent" and "functionally equivalent variant" of a Cas endonuclease or Cas effector protein are used interchangeably herein, and refer to a variant of the Cas effector protein disclosed herein in which the ability to recognize, bind to, and optionally unwind, nick or cleave all or part of a target sequence is retained.

A Cas endonuclease may also include a multifunctional Cas endonuclease. The term "multifunctional Cas endonuclease" and "multifunctional Cas endonuclease polypeptide" are used interchangeably herein and includes reference to a single polypeptide that has Cas endonuclease functionality (comprising at least one protein domain that can act as a Cas endonuclease) and at least one other functionality, such as but not limited to, the functionality to form a cascade (comprises at least a second protein domain that can form a cascade with other proteins). In one aspect, the multifunctional Cas endonuclease comprises at least one additional protein domain relative (either internally, upstream (5'), downstream (3'), or both internally 5' and 3', or any combination thereof) to those domains typical of a Cas endonuclease.

As used herein, the term "guide polynucleotide", relates to a polynucleotide sequence that can form a complex with a Cas endonuclease, including the Cas endonuclease described herein, and enables the Cas endonuclease to recognize, optionally bind to, and optionally cleave a DNA target site. The guide polynucleotide sequence can be a RNA sequence, a DNA sequence, or a combination thereof (a RNA-DNA combination sequence).

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, optionally bind to, and optionally nick or cleave (introduce a single or double-strand break) the DNA target site.

The term "variable targeting domain" or "VT domain" is used interchangeably herein and includes a nucleotide sequence that can hybridize (is complementary) to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a (trans-acting) tracrNucleotide mate sequence followed by a tracrNucleotide sequence. The CER domain can be composed of a DNA sequence, a RNA sequence, a modified DNA sequence, a modified RNA sequence (see for example US20150059010A1, published 26 Feb. 2015), or any combination thereof.

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "Polynucleotide-guided endonuclease", "PGEN" are used interchangeably herein and refer to at least one guide polynucleotide and at least one Cas endonuclease, that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s) and suitable polynucleotide component(s) of any of the known CRISPR systems (Horvath and Barrangou, 2010, *Science* 327:167-170; Makarova et al. 2015, *Nature Reviews Microbiology* Vol. 13:1-15; Zetsche et al., 2015, Cell 163, 1-13; Shmakov et al., 2015, *Molecular Cell* 60, 1-13).

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

The terms "target site", "target sequence", "target site sequence, "target DNA", "target locus", "genomic target site", "genomic target sequence", "genomic target locus", "target polynucleotide", and "protospacer", are used interchangeably herein and refer to a polynucleotide sequence such as, but not limited to, a nucleotide sequence on a chromosome, episome, a locus, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

As used herein, "donor DNA" is a DNA construct that comprises a polynucleotide of interest to be inserted into the target site of a Cas endonuclease.

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The term "plant" generically includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant cells comprise a plant cell wall, and as such are distinct, with different biochemical characteristics, from protoplasts that lack a cell wall.

A "plant element" or "plant part" is intended to reference either a whole plant or a plant component, which may comprise differentiated and/or undifferentiated tissues, for example but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue), plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. The term "plant organ" refers to plant tissue or a group of tissues that constitute a morphologically and functionally distinct part of a plant. As used herein, a "plant element" is synonymous to a "portion" or "part" of a plant, and refers to any part of the plant, and can include distinct tissues and/or organs, and may be used interchangeably with the term "tissue" throughout. Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keiki, or bud. The plant element may be in plant or in a plant organ, tissue culture, or cell culture.

"Progeny" comprises any subsequent generation of a plant.

The term "monocotyledonous" or "monocot" refers to the subclass of angiosperm plants also known as "monocotyledoneae", whose seeds typically comprise only one embryonic leaf, or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants also knows as "dicotyledoneae", whose seeds typically comprise two embryonic leaves, or cotyledons. The term includes references to whole plants, plant elements, plant organs (e.g., leaves, stems, roots, etc.), seeds, plant cells, and progeny of the same.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

The term "isoline" is a comparative term, and references organisms that are genetically identical, but differ in treatment. In one example, two genetically identical maize plant embryos may be separated into two different groups, one receiving a treatment (such as the introduction of a CRISPR-Cas effector endonuclease) and one control that does not receive such treatment. Any phenotypic differences between the two groups may thus be attributed solely to the treatment and not to any inherency of the plant's endogenous genetic makeup.

A "population" of plants refers to a plurality of individual plants that share temporal and spatial location, and may further share one or more characteristic(s), such as a common genotype.

"Introducing" is intended to mean presenting a subject molecule to a target, such as a cell or organism, a polynucleotide or polypeptide or polynucleotide-protein complex, in such a manner that the subject gains access to the target, such as the interior of a cell of the organism or to the cell itself, or in the case of a target polynucleotide, presented to the polynucleotide in such a way that the subject has capability of physical or chemical contact with the polynucleotide.

A "polynucleotide of interest" includes any nucleotide sequence that

In some aspects, a "polynucleotide of interest" encodes a protein or polypeptide that is "of interest" for a particular purpose, e.g. a selectable marker. In some aspects a trait or polynucleotide "of interest" is one that improves a desirable phenotype of a plant, particularly a crop plant, i.e. a trait of agronomic interest. Polynucleotides of interest: include, but are not limited to, polynucleotides encoding important traits for agronomics, herbicide-resistance, insecticidal resistance, disease resistance, nematode resistance, herbicide resistance, microbial resistance, fungal resistance, viral resistance, fertility or sterility, grain characteristics, commercial products, phenotypic marker, or any other trait of agronomic or commercial importance. A polynucleotide of interest may additionally be utilized in either the sense or anti-sense orientation. Further, more than one polynucleotide of interest may be utilized together, or "stacked", to provide additional benefit. In some aspects, a "polynucleotide of interest" may encode a gene expression regulatory element, for example a promoter, intron, terminator, 5'UTR, 3'UTR, or other noncoding sequence. In some aspects, a "polynucleotide of interest" may comprise a DNA sequences that encodes for an RNA molecule, for example a functional RNA, siRNA, miRNA, or a guide RNA that is capable of interacting with a Cas endonuclease to bind to a target polynucleotide sequence.

A "complex trait locus" includes a genomic locus that has multiple transgenes genetically linked to each other.

The compositions and methods herein may provide for an improved "agronomic trait" or "trait of agronomic importance" or "trait of agronomic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

"Agronomic trait potential" is intended to mean a capability of a plant element for exhibiting a phenotype, preferably an improved agronomic trait, at some point during its life cycle, or conveying said phenotype to another plant element with which it is associated in the same plant.

The terms "decreased," "fewer," "slower" and "increased" "faster" "enhanced" "greater" as used herein refers to a decrease or increase in a characteristic of the modified plant element or resulting plant compared to an unmodified plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400%) or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

As used herein, the term "before", in reference to a sequence position, refers to an occurrence of one sequence upstream, or 5', to another sequence.

The meaning of abbreviations is as follows: "sec" means second(s), "min" means minute(s), "h" means hour(s), "d" means day(s), "microliters" means microliter(s), "mL" means milliliter(s), "L" means liter(s), "uM" means micromolar, "mM" means millimolar, "M" means molar, "mmol" means millimole(s), "umole" mean micromole(s), "g" means gram(s), "micrograms" or "ug" means microgram(s), "ng" means nanogram(s), "U" means unit(s), "bp" means base pair(s) and "kb" means kilobase(s).

Cas Endonucleases

Cas Endonucleases and Effectors

Endonucleases are enzymes that cleave the phosphodiester bond within a polynucleotide chain. Examples of endonucleases include restriction endonucleases, meganucleases, TAL effector nucleases (TALENs), zinc finger nucleases, and Cas (CRISPR-associated) effector endonucleases.

Cas endonucleases, either as single effector proteins or in an effector complex with other components, unwind the DNA duplex at the target sequence and optionally cleave at least one DNA strand, as mediated by recognition of the target sequence by a polynucleotide (such as, but not limited to, a crRNA or guide RNA) that is in complex with the Cas endonuclease. Such recognition and cutting of a target sequence by a Cas endonuclease typically occurs if the correct protospacer-adjacent motif (PAM) is located at or adjacent to the 3' end of the DNA target sequence. Alternatively, a Cas endonuclease herein may lack DNA cleavage or nicking activity, but can still specifically bind to a DNA target sequence when complexed with a suitable RNA component. (See also U.S. Patent Application US20150082478 published 19 Mar. 2015 and US20150059010 published 26 Feb. 2015).

Cas endonucleases that have been described include, but are not limited to, for example: Cas3 (a feature of Class 1 type I systems), Cas9 (a feature of Class 2 type II systems) and Cas12 (Cpf1) (a feature of Class 2 type V systems).

Cas9 (formerly referred to as Cas5, Csn1, or Csx12) is a Cas endonuclease that forms a complex with a crNucleotide and a tracrNucleotide, or with a single guide polynucleotide, for specifically recognizing and cleaving all or part of a DNA target sequence. The canonical Cas9 recognizes a 3' GC-rich PAM sequence on the target dsDNA, typically comprising an NGG motif. The Cas endonucleases described herein may recognize additional PAM sequences and used to modify target sites with different recognition sequence specificity.

A Cas9 protein comprises a RuvC nuclease with an HNH (H—N—H) nuclease adjacent to the RuvC-II domain. The RuvC nuclease and HNH nuclease each can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al., 2013, Cell 157:1262-1278). Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA (Makarova et al. 2015, *Nature Reviews Microbiology* Vol. 13:1-15).

Cas endonucleases and effector proteins can be used for targeted genome editing (via simplex and multiplex double-strand breaks and nicks) and targeted genome regulation (via tethering of epigenetic effector domains to either the Cas protein or sgRNA. A Cas endonuclease can also be engineered to function as an RNA-guided recombinase, and via RNA tethers could serve as a scaffold for the assembly of multiprotein and nucleic acid complexes (Mali et al., 2013, *Nature Methods* Vol. 10: 957-963).

A Cas9 endonuclease, effector protein, or functional fragment thereof, for use in the disclosed methods, can be isolated from a native source, or from a recombinant source where the genetically modified host cell is modified to express the nucleic acid sequence encoding the protein. Alternatively, the Cas endonuclease protein can be produced using cell free protein expression systems, or be synthetically produced. Cas endonucleases may be isolated and introduced into a heterologous cell, or may be modified from its native form to exhibit a different type or magnitude of activity than what it would exhibit in its native source. Such modifications include but are not limited to: fragments, variants, substitutions, deletions, and insertions.

Fragments and variants of Cas endonucleases can be obtained via methods such as site-directed mutagenesis and synthetic construction. Methods for measuring endonuclease activity are well known in the art such as, but not limiting to, WO2013166113 published 7 Nov. 2013, WO2016186953 published 24 Nov. 2016, and WO2016186946 published 24 Nov. 2016.

The Cas endonuclease can comprise a modified form of the Cas polypeptide. The modified form of the Cas polypeptide can include an amino acid change (e.g., deletion, insertion, or substitution) that reduces the naturally-occurring nuclease activity of the Cas protein. For example, in some instances, the modified form of the Cas protein has less than 50%, less than 40%, less than 30%, less than 20%, less than 10%, less than 5%, or less than 1% of the nuclease activity of the corresponding wild-type Cas polypeptide (US20140068797 published 6 Mar. 2014). In some cases, the modified form of the Cas polypeptide has no substantial nuclease activity and is referred to as catalytically "inactivated Cas" or "deactivated Cas (dCas)." An inactivated Cas/deactivated Cas includes a deactivated Cas endonuclease (dCas). A catalytically inactive Cas endonuclease can be fused to a heterologous sequence to induce or modify activity.

A Cas endonuclease can be part of a fusion protein comprising one or more heterologous protein domains (e.g., 1, 2, 3, or more domains in addition to the Cas protein. Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas can also be fused to a FokI nuclease to generate double-strand breaks (Guilinger et al. *Nature Biotechnology*, volume 32, number 6, June 2014). In some aspects, the Cas endonuclease is a fusion protein further comprising a nuclease domain, a transcriptional activator domain, a transcriptional repressor domain, an epigenetic modification domain, a cleavage domain, a nuclear localization signal, a cell-penetrating domain, a translocation domain, a marker, or a transgene that is heterologous to the target polynucleotide sequence or to the cell from which said target polynucleotide sequence is obtained or derived. In some aspects, the nuclease fusion protein comprises Clo51 or Fok1.

The Cas endonucleases described herein can be expressed and purified by methods known in the art, for example as described in WO/2016/186953 published 24 Nov. 2016.

In some aspects, one or more Cas endonuclease is a Cas9 endonuclease. Some exemplary Cas9 endonucleases are described, for example, in WO/2019/165168 published 29 Aug. 2019.

A Cas endonuclease can comprise a heterologous nuclear localization sequence (NLS). A heterologous NLS amino acid sequence herein may be of sufficient strength to drive accumulation of a Cas protein in a detectable amount in the nucleus of a yeast cell herein, for example.

Protospacer Adjacent Motif (PAM)

A "protospacer adjacent motif" (PAM) herein refers to a short nucleotide sequence adjacent to a target sequence (protospacer) that can be recognized (targeted) by a guide polynucleotide/Cas endonuclease system. In some aspects, the Cas endonuclease may not successfully recognize a target DNA sequence if the target DNA sequence is not adjacent to, or near, a PAM sequence. In some aspects, the PAM precedes the target sequence (e.g. Cas12a). In some aspects, the PAM follows the target sequence (e.g. *S. pyogenes* Cas9).. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

A "randomized PAM" and "randomized protospacer adjacent motif" are used interchangeably herein, and refer to a random DNA sequence adjacent to a target sequence (protospacer) that is recognized (targeted) by a guide polynucleotide/Cas endonuclease system. The randomized PAM sequence can be of any length but is typically 1, 2, 3, 4, 5, 6, 7, 8, 9, 10, 11, 12, 13, 14, 15, 16, 17, 18, 19 or 20 nucleotides long. A randomized nucleotide includes anyone of the nucleotides A, C, G or T.

Many Cas endonucleases have been described to date that can recognize specific PAM sequences (WO2016186953 published 24 Nov. 2016, WO2016186946 published 24 Nov. 2016, and Zetsche B et al. 2015. Cell 163, 1013) and cleave the target DNA at a specific position. It is understood that based on the methods and embodiments described herein utilizing a novel guided Cas system one skilled in the art can now tailor these methods such that they can utilize any guided endonuclease system.

Guide Polynucleotides

The guide polynucleotide enables target recognition, binding, and optionally cleavage by the Cas endonuclease, and can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (US20150082478 published 19 Mar. 2015 and US20150059010 published 26 Feb. 2015). A guide polynucleotide may be engineered or synthetic.

The guide polynucleotide includes a chimeric non-naturally occurring guide RNA comprising regions that are not found together in nature (i.e., they are heterologous with respect to each other). For example, a chimeric non-naturally occurring guide RNA comprising a first nucleotide sequence domain (referred to as Variable Targeting domain or VT domain) that can hybridize to a nucleotide sequence in a target DNA, linked to a second nucleotide sequence that can recognize the Cas endonuclease, such that the first and second nucleotide sequence are not found linked together in nature.

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences.

In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides.

The tracrRNA (trans-activating CRISPR RNA) comprises, in the 5'-to-3' direction, (i) an "anti-repeat" sequence that anneals with the repeat region of CRISPR type II crRNA and (ii) a stem loop-comprising portion (Deltcheva et al., Nature 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) into the target site. (US20150082478 published 19 Mar. 2015 and US20150059010 published 26 Feb. 2015). In some embodiments, the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides.

In one embodiment, the RNA that guides the RNA/Cas endonuclease complex is a duplexed RNA comprising a duplex crRNA-tracrRNA.

In one aspect, the guide polynucleotide is a guide polynucleotide capable of forming a PGEN as described herein, wherein said guide polynucleotide comprises a first nucleotide sequence domain that is complementary to a nucleotide sequence in a target DNA, and a second nucleotide sequence domain that interacts with said Cas endonuclease polypeptide.

In one aspect, the guide polynucleotide is a guide polynucleotide described herein, wherein the first nucleotide sequence and the second nucleotide sequence domain is selected from the group consisting of a DNA sequence, a RNA sequence, and a combination thereof.

In one aspect, the guide polynucleotide is a guide polynucleotide described herein, wherein the first nucleotide sequence and the second nucleotide sequence domain is selected from the group consisting of RNA backbone modifications that enhance stability, DNA backbone modifications that enhance stability, and a combination thereof (see Kanasty et al., 2013, Common RNA-backbone modifications, *Nature Materials* 12:976-977; US20150082478 published 19 Mar. 2015 and US20150059010 published 26 Feb. 2015)

The guide RNA includes a dual molecule comprising a chimeric non-naturally occurring crRNA linked to at least one tracrRNA. A chimeric non-naturally occurring crRNA includes a crRNA that comprises regions that are not found together in nature (i.e., they are heterologous with each other. For example, a crRNA comprising a first nucleotide sequence domain (referred to as Variable Targeting domain or VT domain) that can hybridize to a nucleotide sequence in a target DNA, linked to a second nucleotide sequence (also referred to as a tracr mate sequence) such that the first and second sequence are not found linked together in nature.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide.

The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) the target site. (US20150082478 published 19 Mar. 2015 and US20150059010 published 26 Feb. 2015).

A chimeric non-naturally occurring single guide RNA (sgRNA) includes a sgRNA that comprises regions that are not found together in nature (i.e., they are heterologous with each other. For example, a sgRNA comprising a first nucleotide sequence domain (referred to as Variable Targeting domain or VT domain) that can hybridize to a nucleotide sequence in a target DNA linked to a second nucleotide sequence (also referred to as a tracr mate sequence) that are not found linked together in nature.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide (also referred to as "loop") can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

The guide polynucleotide can be produced by any method known in the art, including chemically synthesizing guide polynucleotides (such as but not limiting to Hendel et al. 2015, *Nature Biotechnology* 33, 985-989), in vitro generated guide polynucleotides, and/or self-splicing guide RNAs (such as but not limited to Xie et al. 2015, PNAS 112:3570-3575).

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161). This strategy has been successfully applied in cells of several different species including maize and soybean (US 20150082478, published on Mar. 19, 2015). Methods for expressing RNA components that do not have a 5' cap have been described (WO 2016/025131, published on Feb. 18, 2016).

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas9 system that can form a complex with a type II Cas9 endonuclease, wherein said guide RNA/Cas9 endonuclease complex can direct the Cas9 endonuclease to a DNA target site, enabling the Cas9 endonuclease to recognize, bind to, and optionally nick or cleave (introduce a single or double strand break) the DNA target site.

Single guide RNAs targeting a target site in the genome of an organism can be designed by changing the Variable Targeting Domain (VT) of any of the guide polynucleotides described herein, with any random nucleotide that can hybridize to any desired target sequence.

In some embodiments, a subject nucleic acid (e.g., a guide polynucleotide, a nucleic acid comprising a nucleotide sequence encoding a guide polynucleotide; a nucleic acid encoding Cas9 endonuclease of the present disclosure; a crRNA or a nucleotide encoding a crRNA, a tracrRNA or a nucleotide encoding a tracrRNA, a nucleotide encoding a VT domain, a nucleotide encoding a CER domain, etc.) comprises a modification or sequence that provides for an additional desirable feature (e.g., modified or regulated stability; subcellular targeting; tracking, e.g., a fluorescent label; a binding site for a protein or protein complex; etc.). Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

Functional variants of a guide polynucleotide of the present disclosure can comprise a modified guide polynucleotide wherein the modification comprises adding, removing, or otherwise altering loops and/or hairpins in the single guide RNA.

Functional variants of a guide polynucleotide of the present disclosure can comprise a modified guide polynucleotide wherein the modification comprises one or more modified nucleotides in the nucleotide sequence, wherein the one or more modified nucleotides comprises at least one non-naturally-occurring nucleotide, nucleotide mimetic (as described in US application US2014/0068797, published Mar. 6, 2014), or analog thereof, or wherein the one or more modified nucleotides are selected from the group consisting of 2'-0-methylanalogs, 2'-fluoro analogs 2-aminopurine, 5-bromo-uridine, pseudouridine, and 7-methylguanosine.

In one aspect, the functional variant of the guide RNA can form a guide RNA/Cas9 endonuclease complex that can recognize, bind to, and optionally nick or cleave a target sequence.

Guide Polynucleotide/Cas Endonuclease Complexes

A guide polynucleotide/Cas endonuclease complex described herein is capable of recognizing, binding to, and optionally nicking, unwinding, or cleaving all or part of a target sequence.

A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas protein disclosed herein), or a variant thereof retaining some or all activity in each endonuclease domain of the Cas protein, is a suitable example of a Cas endonuclease that can cleave both strands of a DNA target sequence.

A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas nickase may comprise (i) a mutant, dysfunctional RuvC domain and (ii) a functional HNH domain (e.g., wild type HNH domain). As another example, a Cas nickase may comprise (i) a functional RuvC domain (e.g., wild type RuvC domain) and (ii) a mutant, dysfunctional HNH domain. Non-limiting examples of Cas nickases suitable for use herein are disclosed in US20140189896 published on 3 Jul. 2014. A pair of Cas nickases can be used to increase the specificity of DNA targeting. In general, this can be done by providing two Cas nickases that, by virtue of being associated with RNA components with different guide sequences, target and nick nearby DNA sequences on opposite strands in the region for desired targeting. Such nearby cleavage of each DNA strand creates a double-strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least 5, between 5 and 10, at least 10, between 10 and 15, at least 15, between 15 and 20, at least 20, between 20 and 30, at least 30, between 30 and 40, at least 40, between 40 and 50, at least 50, between 50 and 60, at least 60, between 60 and 70, at least 70, between 70 and 80, at least 80, between 80 and 90, at least 90, between 90 and 100, or 100 or greater (or any number between 5 and 100) bases apart from each other, for example. One or two Cas nickase proteins herein can be used in a Cas nickase pair. For example, a Cas nickase with a mutant RuvC domain, but functioning HNH domain (i.e., Cas HNH+/RuvC−), can be used (e.g., *Streptococcus pyogenes* Cas HNH+/RuvC−). Each Cas nickase (e.g., Cas HNH+/RuvC−) can be directed to specific DNA sites nearby each other (up to 100 base pairs apart) by using suitable RNA components herein with guide RNA sequences targeting each nickase to each specific DNA site.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas protein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein).

In one embodiment of the disclosure, the guide polynucleotide/Cas endonuclease complex is a guide polynucleotide/Cas endonuclease complex (PGEN) comprising at least one guide polynucleotide and at least one Cas endonuclease polypeptide. In some aspects, the Cas endonuclease polypeptide comprises at least one protein subunit of another Cas protein, or a functional fragment thereof, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.

In some aspects, the PGEN is a ribonucleoprotein complex (RNP), wherein the Cas endonuclease is provided as a protein and the guide polynucleotide is provided as a ribonucleotide.

In one embodiment of the disclosure, the guide polynucleotide/Cas effector complex is a guide polynucleotide/Cas endonuclease complex (PGEN) comprising at least one guide polynucleotide and a Cas endonuclease endonuclease, wherein said guide polynucleotide/Cas endonuclease complex is capable of recognizing, binding to, and optionally nicking, unwinding, or cleaving all or part of a target sequence.

The PGEN can be a guide polynucleotide/Cas endonuclease complex, wherein said Cas endonuclease further comprises one copy or multiple copies of at least one protein subunit, or a functional fragment thereof, of an additional Cas protein.

In one aspect, the guide polynucleotide/Cas endonuclease complex (PGEN) described herein is a PGEN, wherein said Cas endonuclease is covalently or non-covalently linked to at least one Cas protein subunit, or functional fragment thereof. The PGEN can be a guide polynucleotide/Cas endonuclease complex, wherein said Cas endonuclease polypeptide is covalently or non-covalently linked, or assembled to one copy or multiple copies of at least one protein subunit, or a functional fragment thereof, of a Cas protein selected from the group consisting of a Cas1 protein subunit, a Cas2 protein subunit, a Cas4 protein subunit, and any combination thereof, in some aspects effectively forming a cleavage ready Cascade. The PGEN can be a guide polynucleotide/Cas endonuclease complex, wherein said Cas endonuclease is covalently or non-covalently linked or assembled to at least two different protein subunits of a Cas protein selected from the group consisting of a Cas1, a Cas2, and Cas4. The PGEN can be a guide polynucleotide/Cas endonuclease complex, wherein said Cas endonuclease is covalently or non-covalently linked to at least three different protein subunits, or functional fragments thereof, of a Cas protein selected from the group consisting of a Cas1, a Cas2, and Cas4, and any combination thereof.

Any component of the guide polynucleotide/Cas endonuclease complex, the guide polynucleotide/Cas endonuclease complex itself, as well as the polynucleotide modification template(s) and/or donor DNA(s), can be introduced into a heterologous cell or organism by any method known in the art.

Some uses for guide RNA/Cas9 endonuclease systems include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods and compositions are provided herein for the chemical modification or alteration of one or more nucleobases of a target polynucleotide, to change the base(s) from one type to another, for example from a Cytosine to a Thymine or an Adenine to a Guanine, using an RNA-guided Cas endonuclease that has been modified to lack double- or single-strand cleaving activity.

Base Editing

One or more nucleobases of a target polynucleotide can be chemically altered, in some cases to change the base from one type to another, for example from a Cytosine to a Thymine, or an Adenine to a Guanine. In some aspects, a plurality of bases, for example 2 or more, 5 or more, 10 or more, 20 or more, 30 or more, 40 or more, 50 or more, 60 or more, 70 or more, 80 or more 90 or more, 100 or more, or even greater than 100, 200 or more, up to thousands of bases may be modified or altered, to produce a plant with a plurality of modified bases.

Any base editing complex, such as a base editing agent associated with an RNA-guided protein, may be used to target and bind to a desired locus in the genome of an organism and chemically modify one or more components of a target polynucleotide.

Site-specific base conversions can be achieved to engineer one or more nucleotide changes to create one or more edits into the genome. These include for example, a site-specific base edit mediated by an C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. A catalytically "dead" or inactive Cas9 (dCas9), for example a catalytically inactive "dead" version of a Cas endonuclease disclosed herein, fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA. Any molecule that effects a change in a nucleobase is a "base editing agent".

For many traits of interest, the creation of single double-strand breaks and the subsequent repair via HDR or NHEJ is not ideal for quantitative traits. An observed phenotype includes both genotype effects and environmental effects. The genotype effects further comprise additive effects, dominance effects, and epistatic effects. The probability of no effect per any single edit can be greater than zero, and any single phenotypic effect can be small, depending on the method used and site selected. Double-stranded break repair can additionally be "noisy" and have low repeatability.

One approach to ameliorate the probability of no effect per edit or small phenotypic effect outcome is to multiplex genome modification, such that a plurality of target sites are modified. Methods to modify a genomic sequence that do not introduce double-strand breaks would allow for single base substitutions. Combining these approaches, multiplexed base editing is beneficial for creating large numbers of genotype edits that can produce observable phenotype modifications. In some cases, dozens or hundreds or thousands of sites can be edited within one or a few generations of an organism.

A multiplexed approach to base editing in an organism, has the potential to create a plurality of significant phenotypic variations in one or a few generations, with a positive directional bias to the effects. In some aspects, the organism is a plant. A plant or a population of plants with a plurality of edits can be cross-bred to produce progeny plants, some of which will comprise multiple pluralities of edits from the parental lines. In this way, accelerated breeding of desired traits can be accomplished in parallel in one or a few generations, replacing time-consuming traditional sequential crossing and breeding across multiple generations.

A base editing deaminase, such as a cytidine deaminase or an adenine deaminase, may be fused to an RNA-guided endonuclease that can be deactivated ("dCas", such as a deactivated Cas9) or partially active ("nCas", such as a Cas9 nickase) so that it does not cleave a target site to which it is guided. The dCas forms a functional complex with a guide polynucleotide that shares homology with a polynucleotide sequence at the target site, and is further complexed with the deaminase molecule. The guided Cas endonuclease recognizes and binds to a double-stranded target sequence, opening the double-strand to expose individual bases. In the case of a cytidine deaminase, the deaminase deaminates the cytosine base and creates a uracil. Uracil glycosylase inhibitor (UGI) is provided to prevent the conversion of U back to C. DNA replication or repair mechanisms then convert the Uracil to a thymine (U to T), and subsequent repair of the opposing base (formerly G in the original G-C pair) to an Adenine, creating a T-A pair. For example, see Komor et al. Nature Volume 533, Pages 420-424, 19 May 2016.

Evaluation and Selection of Target Sites

The length of the DNA sequence at the target site can vary, and includes, for example, target sites that are at least 12, 13, 14, 15, 16, 17, 18, 19, 20, 21, 22, 23, 24, 25, 26, 27, 28, 29, 30, or more than 30 nucleotides in length. It is further possible that the target site can be palindromic, that is, the sequence on one strand reads the same in the opposite direction on the complementary strand.

Any cell genome can be evaluated for potential target sites for multiplexed base editing. In one non-limiting example, an elite inbred line of a particular plant is selected, wherein the elite inbred line displays one or more desirable phenotypes. However, the elite inbred line may further comprise some alleles that can be optimized. Candidate editing sites are selected via one of several methods that identifies such optimizable alleles, that may be neutral or deleterious in the original genome but positive, beneficial, or desirable after editing, such as with a deaminase base editor.

Any approach or combination of approaches may be used to find candidate sites in a genome for multiple site editing, for example but not limited to: evolutionary conservation, computational functional prediction, or candidate QTNs identified from experimentation or the literature. Because single edit effects are likely to be small, multiplexing of the edits is an important feature. In some cases, individual phenotypes affected may not be obvious, but fitness association would likely impact yield components of a plant.

In one approach, calculations of evolutionary conservation of individual nucleotides are performed and evaluated, such as Genomic Evolutionary Rate Profiling (GERP), which is a method for producing position-specific estimates of evolutionary constraint using maximum likelihood evolutionary rate estimation. Several "constrained elements" where multiple positions combine to give a signal that is indicative of a putative functional element are identified; this track shows the position-specific scores only, not the element predictions. Constraint intensity at each individual alignment position is quantified in terms of a "rejected substitutions" (RS) score, defined as the number of substitutions expected under neutrality minus the number of substitutions "observed" at the position.

Genomic sites for potential editing are scored independently. Positive scores represent a substitution deficit (i.e., fewer substitutions than the average neutral site) and thus indicate that a site may be under evolutionary constraint. Negative scores indicate that a site is probably evolving neutrally; negative scores should not be interpreted as evidence of accelerated rates of evolution because of too many strong confounders, such as alignment uncertainty or rate variance. Positive scores scale with the level of constraint, such that the greater the score, the greater the level of evolutionary constraint inferred to be acting on that site.

Potential sites for selection for editing, including base editing, are made of alleles at evolutionarily conserved loci that display nucleotide positions that are different than the consensus across multiple genomes. In plants, incomplete dominance of deleterious alleles contributes to trait variation and heterosis in maize.

In another method, candidate edits can be selected based on attention-based predictor network algorithms. Sites with a mutation increasing expression levels of a gene are more conserved, while sites with a mutation decreasing expression levels of a gene are less conserved. For example, conserved sites with a particular allele that has predicted regulatory effects could be one target for base editing.

Identification of candidate alleles for editing can be, for example but not limited to, non-conserved bases in a particular cell line at a conserved (polymorphic) site, bases producing nonsense codons, and/or predicted rare nonsynonymous high impact substitutions.

Recombinant Constructs for Transformation of Cells

The disclosed guide polynucleotides, Cas endonucleases, deaminases, and guide various molecular systems disclosed herein, and any one combination thereof, optionally further comprising one or more polynucleotide(s) or polypeptide(s) of interest, can be introduced into a cell. Cells include, but are not limited to, human, non-human, animal, bacterial, fungal, insect, yeast, non-conventional yeast, and plant cells as well as plants and seeds produced by the methods described herein.

Standard recombinant DNA and molecular cloning techniques used herein are well known in the art and are described more fully in Sambrook et al., *Molecular Cloning: A LaboratoryManual; Cold Spring Harbor Laboratory*: Cold Spring Harbor, NY (1989). Transformation methods are well known to those skilled in the art and are described infra.

Vectors and constructs include circular plasmids, and linear polynucleotides, comprising a polynucleotide of interest and optionally other components including linkers, adapters, regulatory or analysis. In some examples a recognition site and/or target site can be comprised within an intron, coding sequence, 5' UTRs, 3' UTRs, and/or regulatory regions.

Components for Expression and Utilization of CRISPR-Cas Systems in Prokaryotic and Eukaryotic cells The invention further provides expression constructs for expressing in a prokaryotic or eukaryotic cell/organism a guide RNA/Cas system that is capable of recognizing, binding to, and optionally nicking, unwinding, or cleaving all or part of a target sequence.

In one embodiment, the expression constructs of the disclosure comprise a promoter operably linked to a nucleotide sequence encoding a Cas gene (or optimized sequence, including a Cas endonuclease gene described herein) and a promoter operably linked to a guide RNA of the present disclosure. The promoter is capable of driving expression of an operably linked nucleotide sequence in a prokaryotic or eukaryotic cell/organism.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

Expression Elements

Any polynucleotide encoding a Cas endonuclease, guide RNA, or other CRISPR system component disclosed herein may be functionally linked to a heterologous expression element, to facilitate transcription or regulation in a host cell. Such expression elements include but are not limited to: promoter, leader, intron, and terminator. Expression elements may be "minimal"—meaning a shorter sequence derived from a native source, that still functions as an expression regulator or modifier. Alternatively, an expression element may be "optimized"-meaning that its polynucleotide sequence has been altered from its native state in order to function with a more desirable characteristic in a particular host cell. Alternatively, an expression element may be "synthetic"—meaning that it is designed in silico and synthesized for use in a host cell. Synthetic expression elements may be entirely synthetic, or partially synthetic (comprising a fragment of a naturally-occurring polynucleotide sequence).

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). This strategy has been successfully applied in cells of several different species including maize and soybean (US20150082478 published 19 Mar. 2015). Methods for expressing RNA components that do not have a 5' cap have been described (WO2016/025131 published 18 Feb. 2016).

Optimization of Sequences for Expression in Plants

Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

Polynucleotides of Interest

Polynucleotides of interest may be endogenous to the organism being edited, or maybe provided as heterologous molecules to the organism.

General categories of polynucleotides of interest include, for example, genes of interest involved in information, such as zinc fingers, those involved in communication, such as kinases, and those involved in housekeeping, such as heat shock proteins. More specific polynucleotides of interest include, but are not limited to, genes involved in crop yield, grain quality, crop nutrient content, starch and carbohydrate quality and quantity as well as those affecting kernel size, sucrose loading, protein quality and quantity, nitrogen fixation and/or utilization, fatty acid and oil composition, genes encoding proteins conferring resistance to abiotic stress (such as drought, nitrogen, temperature, salinity, toxic metals or trace elements, or those conferring resistance to molecules such as pesticides or herbicides), genes encoding proteins conferring resistance to biotic stress (such as attacks by fungi, viruses, bacteria, insects, or nematodes, and development of diseases associated with these organisms).

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch.

Polynucleotide sequences of interest may encode proteins involved in providing disease or pest resistance. By "disease resistance" or "pest resistance" is intended that the plants avoid the harmful symptoms that are the outcome of the plant-pathogen interactions.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS, also referred to as acetohydroxyacid synthase, AHAS), in particular the sulfonylurea (UK: sulphonylurea) type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and 9,187,762. The bar gene encodes resistance to the herbicide basta, the nptII gene encodes resistance to the antibiotics kanamycin and geneticin, and the ALS-gene mutants encode resistance to the herbicide chlorsulfuron.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that comprises it, often under particular conditions. These markers can encode an activity, such as, but not limited to, production of RNA, peptide, or protein, or can provide a binding site for RNA, peptides, proteins, inorganic and organic compounds or compositions and the like.

Introduction of CRISPR-Cas System Components into a Cell

The methods and compositions described herein do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a nucleic acid, protein or polynucleotide-protein complex (PGEN, RGEN) to the cell.

Methods for introducing polynucleotides or polypeptides or a polynucleotide-protein complex into cells or organisms are known in the art including, but not limited to, microinjection, electroporation, stable transformation methods, transient transformation methods, ballistic particle acceleration (particle bombardment), whiskers mediated transformation, *Agrobacterium*-mediated transformation, direct gene transfer, viral-mediated introduction, transfection, transduction, cell-penetrating peptides, mesoporous silica nanoparticle (MSN)-mediated direct protein delivery, topical applications, sexual crossing, sexual breeding, and any combination thereof.

For example, the guide polynucleotide (guide RNA, crNucleotide+tracrNucleotide, guide DNA and/or guide RNA-DNA molecule) can be introduced into a cell directly (transiently) as a single stranded or double stranded polynucleotide molecule. The guide RNA (or crRNA+tracrRNA) can also be introduced into a cell indirectly by introducing a recombinant DNA molecule comprising a heterologous nucleic acid fragment encoding the guide RNA (or crRNA+tracrRNA), operably linked to a specific promoter that is capable of transcribing the guide RNA (crRNA+tracrRNA molecules) in said cell. The specific promoter can be, but is not limited to, a RNA polymerase III promoter, which allow for transcription of RNA with precisely defined, unmodified, 5'- and 3'-ends (Ma et al., 2014, *Mol. Ther. Nucleic Acids* 3:e161; DiCarlo et al., 2013, *Nucleic Acids Res.* 41: 4336-4343; WO2015026887, published 26 Feb. 2015). Any promoter capable of transcribing the guide RNA in a cell can be used and includes a heat shock/heat inducible promoter operably linked to a nucleotide sequence encoding the guide RNA.

The Cas endonuclease, such as the Cas endonuclease described herein, can be introduced into a cell by directly introducing the Cas polypeptide itself (referred to as direct delivery of Cas endonuclease), the mRNA encoding the Cas protein, and/or the guide polynucleotide/Cas endonuclease complex itself, using any method known in the art. The Cas endonuclease can also be introduced into a cell indirectly by introducing a recombinant DNA molecule that encodes the Cas endonuclease. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in WO2016073433 published 12 May 2016. Any promoter capable of expressing the Cas endonuclease in a cell can be used and includes a heat shock/heat inducible promoter operably linked to a nucleotide sequence encoding the Cas endonuclease.

Direct delivery of a polynucleotide modification template into plant cells can be achieved through particle mediated delivery, and any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in eukaryotic cells, such as plant cells.

Direct delivery of any one of the guided Cas system components can be accompanied by direct delivery (co-delivery) of other mRNAs that can promote the enrichment and/or visualization of cells receiving the guide polynucleotide/Cas endonuclease complex components. For example, direct co-delivery of the guide polynucleotide/Cas endonuclease components (and/or guide polynucleotide/Cas endonuclease complex itself) together with mRNA encoding phenotypic markers (such as but not limiting to transcriptional activators such as CRC (Bruce et al. 2000 *The Plant Cell* 12:65-79) can enable the selection and enrichment of cells without the use of an exogenous selectable marker by restoring function to a non-functional gene product as described in WO2017070032 published 27 Apr. 2017.

Introducing a guide RNA/Cas endonuclease complex described herein, into a cell includes introducing the individual components of said complex either separately or combined into the cell, and either directly (direct delivery as RNA for the guide and protein for the Cas endonuclease and Cas protein subunits, or functional fragments thereof) or via recombination constructs expressing the components (guide RNA, Cas endonuclease, Cas protein subunits, or functional fragments thereof). Introducing a guide RNA/Cas endonuclease complex (RGEN) into a cell includes introducing the guide RNA/Cas endonuclease complex as a ribonucleotide-protein into the cell. The ribonucleotide-protein can be assembled prior to being introduced into the cell as described herein. The components comprising the guide RNA/Cas endonuclease ribonucleotide protein (at least one Cas endonuclease, at least one guide RNA, at least one Cas protein subunits) can be assembled in vitro or assembled by any means known in the art prior to being introduced into a cell (targeted for genome modification as described herein).

Plant cells differ from human and animal cells in that plant cells comprise a plant cell wall which may act as a barrier to the direct delivery of the RGEN ribonucleoproteins and/or of the direct delivery of the RGEN components.

Direct delivery of the RGEN ribonucleoproteins into plant cells can be achieved through particle mediated delivery (particle bombardment. Based on the experiments described herein, a skilled artesian can now envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RGEN ribonucleoproteins into plant cells.

Direct delivery of the RGEN ribonucleoprotein, allows for genome editing at a target site in the genome of a cell which can be followed by rapid degradation of the complex, and only a transient presence of the complex in the cell. This transient presence of the RGEN complex may lead to reduced off-target effects. In contrast, delivery of RGEN components (guide RNA, Cas endonuclease) via plasmid DNA sequences can result in constant expression of RGENs from these plasmids which can intensify off target effects (Cradick, T. J. et al. (2013) *Nucleic Acids Res* 41:9584-9592; Fu, Y et al. (2014) *Nat. Biotechnol.* 31:822-826).

Direct delivery can be achieved by combining any one component of the guide RNA/Cas endonuclease complex (RGEN) (such as at least one guide RNA, at least one Cas protein, and at least one Cas protein), with a particle delivery matrix comprising a microparticle (such as but not limited to of a gold particle, tungsten particle, and silicon carbide whisker particle) (see also WO2017070032 published 27 Apr. 2017).

In one aspect, the guide polynucleotide/Cas endonuclease complex is a complex wherein the guide RNA and Cas endonuclease protein forming the guide RNA/Cas endonuclease complex are introduced into the cell as RNA and protein, respectively.

In one aspect, the guide polynucleotide/Cas endonuclease complex is a complex wherein the guide RNA and Cas endonuclease protein and the at least one protein subunit of a Cas protein forming the guide RNA/Cas endonuclease complex are introduced into the cell as RNA and proteins, respectively.

In one aspect, the guide polynucleotide/Cas endonuclease complex is a complex wherein the guide RNA and Cas endonuclease protein and the at least one protein subunit of a Cascade forming the guide RNA/Cas endonuclease complex (cleavage ready cascade) are preassembled in vitro and introduced into the cell as a ribonucleotide-protein complex.

Protocols for introducing polynucleotides, polypeptides or polynucleotide-protein complexes (PGEN, RGEN) into eukaryotic cells, such as plants or plant cells are known.

Alternatively, polynucleotides may be introduced into plant or plant cells by contacting cells or organisms with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

The polynucleotide or recombinant DNA construct can be provided to or introduced into a prokaryotic and eukaryotic cell or organism using a variety of transient transformation methods. Such transient transformation methods include, but are not limited to, the introduction of the polynucleotide construct directly into the plant.

Nucleic acids and proteins can be provided to a cell by any method including methods using molecules to facilitate the uptake of anyone or all components of a guided Cas system (protein and/or nucleic acids), such as cell-penetrating peptides and nanocarriers. See also US20110035836 published 10 Feb. 2011, and EP2821486A1 published 7 Jan. 2015.

Other methods of introducing polynucleotides into a prokaryotic and eukaryotic cell or organism or plant part can be used, including plastid transformation methods, and the methods for introducing polynucleotides into tissues from seedlings or mature seeds.

Stable transformation is intended to mean that the nucleotide construct introduced into an organism integrates into a genome of the organism and is capable of being inherited by the progeny thereof. Transient transformation is intended to mean that a polynucleotide is introduced into the organism and does not integrate into a genome of the organism or a polypeptide is introduced into an organism. Transient transformation indicates that the introduced composition is only temporarily expressed or present in the organism.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The presently disclosed polynucleotides and polypeptides can be introduced into a cell. Cells include, but are not limited to, human, non-human, animal, mammalian, bacterial, protist, fungal, insect, yeast, non-conventional yeast, and plant cells, as well as plants and seeds produced by the methods described herein. In some aspects, the cell of the organism is a reproductive cell, a somatic cell, a meiotic cell, a mitotic cell, a stem cell, or a pluripotent stem cell.

Cells and Plants

The presently disclosed polynucleotides and polypeptides can be introduced into a plant cell. Plant cells include, well as plants and seeds produced by the methods described herein. Any plant can be used with the compositions and methods described herein, including monocot and dicot plants, and plant elements.

The novel Cas endonucleases disclosed may be used to edit the genome of a plant cell in various ways. In one aspect, it may be desirable to delete one or more nucleotides. In another aspect, it may be desirable to insert one or more nucleotides. In one aspect, it may be desirable to replace one or more nucleotides. In another aspect, it may be desirable to modify one or more nucleotides via a covalent or non-covalent interaction with another atom or molecule. In some aspects, the cell is diploid. In some aspects, the cell is haploid.

Genome modification via a Cas endonuclease may be used to effect a genotypic and/or phenotypic change on the target organism. Such a change is preferably related to an improved trait of interest or an agronomically-important characteristic, the correction of an endogenous defect, or the expression of some type of expression marker. In some aspects, the trait of interest or agronomically-important characteristic is related to the overall health, fitness, or fertility of the plant, the yield of a plant product, the ecological fitness of the plant, or the environmental stability of the plant. In some aspects, the trait of interest or agronomically-important characteristic is selected from the group consisting of: agronomics, herbicide resistance, insecticide resistance, disease resistance, nematode resistance, microbial resistance, fungal resistance, viral resistance, fertility or sterility, grain characteristics, commercial product production. In some aspects, the trait of interest or agronomically-important characteristic is selected from the group consisting of: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered starch content, altered carbohydrate content, altered sugar content, altered fiber content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum* species, for example *Triticum aestivum, Triticum monococcum*), sugarcane (*Saccharum* spp.), oats (*Avena*), barley (*Hordeum*), switchgrass (*Panicum virgatum*), pineapple (*Ananas comosus*), banana (Musa spp.), palm, ornamentals, turfgrasses, and other grasses.

Examples of dicot plants that can be used include, but are not limited to, soybean (*Glycine max*), *Brassica* species (for example but not limited to: oilseed rape or Canola) (*Brassica napus, B. campestris, Brassica rapa, Brassica juncea*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum, Gossypium barbadense*), and peanut (*Arachis hypogaea*), tomato (*Solanum lycopersicum*), potato (*Solanum tuberosum*).

Additional plants that can be used include safflower (Carthamus tinctorius), sweet potato (*Ipomoea batatus*), cassava (*Manihot esculenta*), coffee (*Coffea* spp.), coconut (*Cocos nucifera*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), vegetables, ornamentals, and conifers.

Vegetables that can be used include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum.*

Conifers that may be used include pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow cedar (*Chamaecyparis nootkatensis*).

In certain embodiments of the disclosure, a fertile plant is a plant that produces viable male and female gametes and is self-fertile. Such a self-fertile plant can produce a progeny plant without the contribution from any other plant of a gamete and the genetic material comprised therein. Other embodiments of the disclosure can involve the use of a plant that is not self-fertile because the plant does not produce male gametes, or female gametes, or both, that are viable or otherwise capable of fertilization.

The present disclosure finds use in the breeding of plants comprising one or more edited alleles created by the methods or compositions disclosed herein. In some aspects, the edited alleles influence the phenotypic expression of one or more traits, such as plant health, growth, or yield. In some aspects, two plants may be crossed via sexual reproduction to create progeny plant(s) that comprise some or all of the edits from both parental plants.

Cells and Animals

The presently disclosed polynucleotides and polypeptides can be introduced into an animal cell. Animal cells can include, but are not limited to: an organism of a phylum including chordates, arthropods, mollusks, annelids, cnidarians, or echinoderms; or an organism of a class including mammals, insects, birds, amphibians, reptiles, or fishes. In some aspects, the animal is human, mouse, *C. elegans*, rat, fruit fly (*Drosophila* spp.), zebrafish, chicken, dog, cat, guinea pig, hamster, chicken, Japanese ricefish, sea lamprey, pufferfish, tree frog (e.g., *Xenopus* spp.), monkey, or chimpanzee. Particular cell types that are contemplated include haploid cells, diploid cells, reproductive cells, neurons, muscle cells, endocrine or exocrine cells, epithelial cells, muscle cells, tumor cells, embryonic cells, hematopoietic cells, bone cells, germ cells, somatic cells, stem cells, pluripotent stem cells, induced pluripotent stem cells, progenitor cells, meiotic cells, and mitotic cells. In some aspects, a plurality of cells from an organism may be used.

The novel Cas endonucleases disclosed may be used to edit the genome of an animal cell in various ways. In one aspect, it may be desirable to delete one or more nucleotides. In another aspect, it may be desirable to insert one or more nucleotides. In one aspect, it may be desirable to replace one or more nucleotides. In another aspect, it may be desirable to modify one or more nucleotides via a covalent or non-covalent interaction with another atom or molecule.

Genome modification via a Cas endonuclease may be used to effect a genotypic and/or phenotypic change on the target organism. Such a change is preferably related to an improved phenotype of interest or a physiologically-important characteristic, the correction of an endogenous defect, or the expression of some type of expression marker. In some aspects, the phenotype of interest or physiologically-important characteristic is related to the overall health, fitness, or fertility of the animal, the ecological fitness of the animal, or the relationship or interaction of the animal with other organisms in its environment. In some aspects, the phenotype of interest or physiologically-important characteristic is selected from the group consisting of: improved general health, disease reversal, disease modification, disease stabilization, disease prevention, treatment of parasitic infections, treatment of viral infections, treatment of retroviral infections, treatment of bacterial infections, treatment of neurological disorders (for example but not limited to: multiple sclerosis), correction of endogenous genetic defects (for example but not limited to: metabolic disorders, Achondroplasia, Alpha-1 Antitrypsin Deficiency, Antiphospholipid Syndrome, Autism, Autosomal Dominant Polycystic Kidney Disease, Barth syndrome, Breast cancer, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis Imperfecta, Parkinson's disease, Phenylketonuria, Poland Anomaly, Porphyria, Progeria, Prostate Cancer, Retinitis Pigmentosa, Severe Combined Immunodeficiency (SCID), Sickle cell disease, Skin Cancer, Spinal Muscular Atrophy, Tay-Sachs, Thalassemia, Trimethylaminuria, Turner Syndrome, Velocardiofacial Syndrome, WAGR Syndrome, and Wilson Disease), treatment of innate immune disorders (for example but not limited to: immunoglobulin subclass deficiencies), treatment of acquired immune disorders (for example but not limited to: AIDS and other HIV-related disorders), treatment of cancer, as well as treatment of diseases, including rare or "orphan" conditions, that have eluded effective treatment options with other methods.

Cells that have been genetically modified using the compositions or methods disclosed herein may be transplanted to a subject for purposes such as gene therapy, e.g. to treat a disease, or as an antiviral, antipathogenic, or anticancer therapeutic, for the production of genetically modified organisms in agriculture, or for biological research.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific embodiments of some aspects of the invention. The examples are offered for illustrative purposes only, and are not intended to limit the scope of the invention in any way.

Although maize was used for exemplary purposes, the methods described herein may be utilized for any organism, such as any plant, such as any monocot or dicot.

Example 1: Identification of Candidate Alleles/Bases for Editing

This example demonstrates the selection of putatively deleterious missense alleles for editing by a base editor within a target genome. Although the example described pertains to a cytosine deaminase, the use of an alternative base editor (e.g. adenine deaminase) may be facilitated by substitution of the target base configuration.

Figure 3:
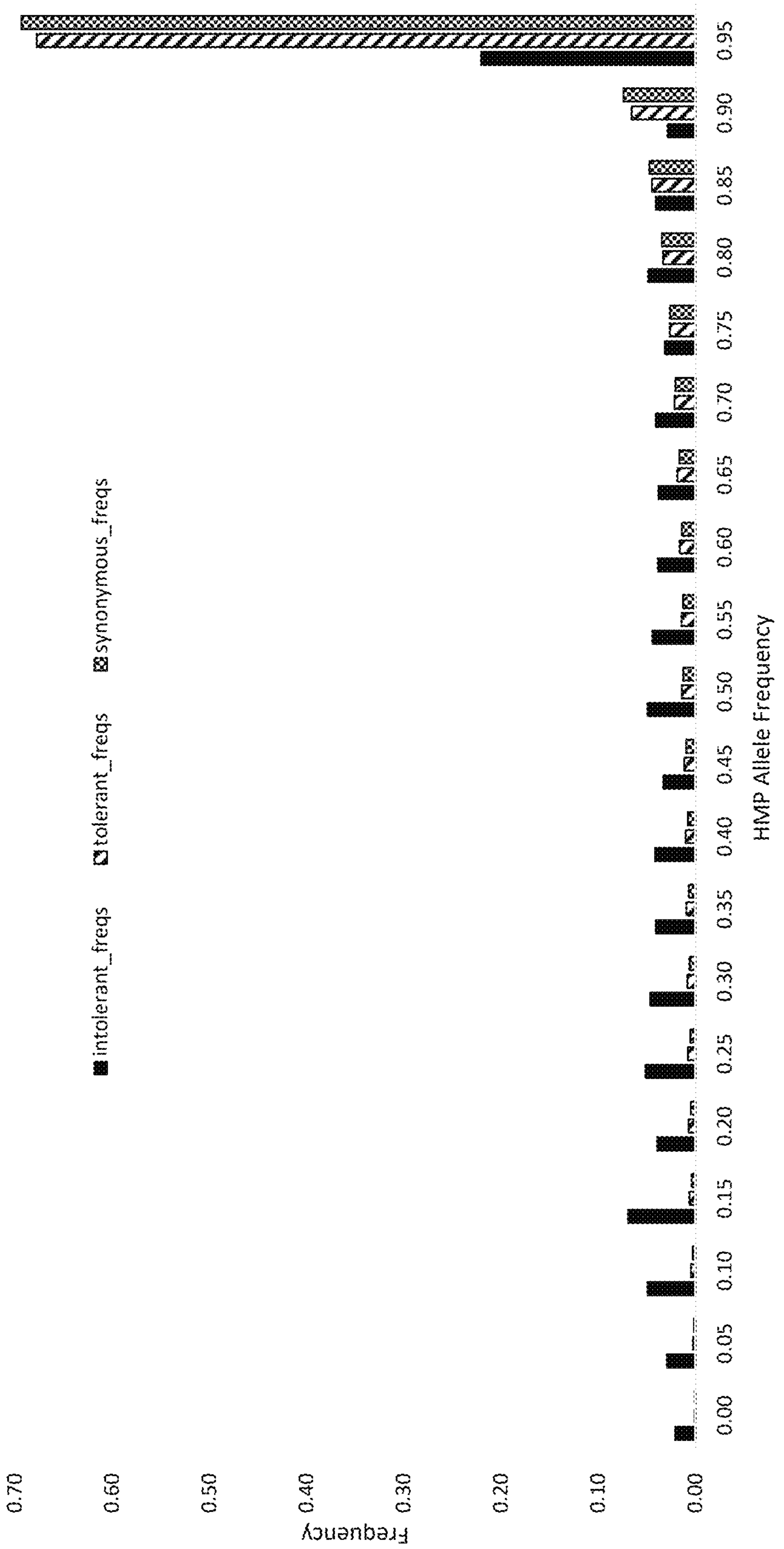
FIG. 3 depicts Target genome allele frequencies of candidate sites in maize (intolerant missense) characterized by maize HapMap3 allele frequencies, compared to tolerant missense and synonymous alleles from the same target genome. Candidate sites show a strong enrichment for rare alleles, despite not using allele frequency as a screening criterion.

To discover putatively deleterious missense mutation amenable to editing with a cytosine deaminase base editor, all sites within the target genome that corresponded to known polymorphic sites in maize were screened, using a combination of a single nucleotide polymorphism (SNP) dataset and a HapMap3 SNP dataset of 1,218 *Zea mays* lines (Bukowski et al. 2018). Sites annotated as polymorphic with maize and occurring within annotated coding sequence were then checked against the SIFT 4G database for *Z. mays* (Vaser et al. 2016), which uses amino acid conservation within a multiple species alignment to provide scores denoting whether base substitutions are likely to be tolerated or selected against. The resulting sites and their SIFT scores were then filtered to those amendable to "fixing" the putative deleterious missense alleles via C→T base editing. Specifically, C and G alleles in the target genomes with a SIFT score of 0.075 or lower that corresponded to, respectively, segregating T and A alleles with SIFT scores of 0.4 or higher were selected as candidate editing sites. The specific thresholds of 0.075 and 0.4 were chosen to balance the needs for a useful enrichment of deleterious alleles with a sufficient quantity to test multiplexing capability, and these may be adjusted as needed. Furthermore, target alleles were checked for their frequencies within the HapMap3 dataset, with rarer alleles prioritized for editing. Overall, candidate sites were found to have a strong enrichment for rare alleles compared to both putatively non-deleterious missense mutations and synonymous mutations (FIG. 3).

Following the selection of the initial candidate sites, additional screening was carried out to fulfill the PAM requirements of the Cas9 construct, avoid editing of redundant target bases within the editing window, and minimize off-target editing. As initial experiments were carried out using the *S. pyogenes* Cas9, sites were screened for an NGG PAM motif with the assumption of an sgRNA length of 20 and a target window of 5-7 bp (14-16 bp from the PAM). Additionally, candidate sites were discarded if a redundant copy of the target allele was present within the editing window. Finally, sites were screened for sufficient uniqueness in the genome using BLAST, and those with too many hits within a specified editing distance were discarded.

The use of an adenine base editor, which induces the conversion of A to G (T to C) nucleotides, provides the additional opportunity to fix nonsense mutations resulting from a base substitution producing a stop codon within an open reading frame. Such nonsense mutations have a high probability of producing deleterious fitness effects and therefore provide an excellent initial candidate set for base editing.

Figure 4:
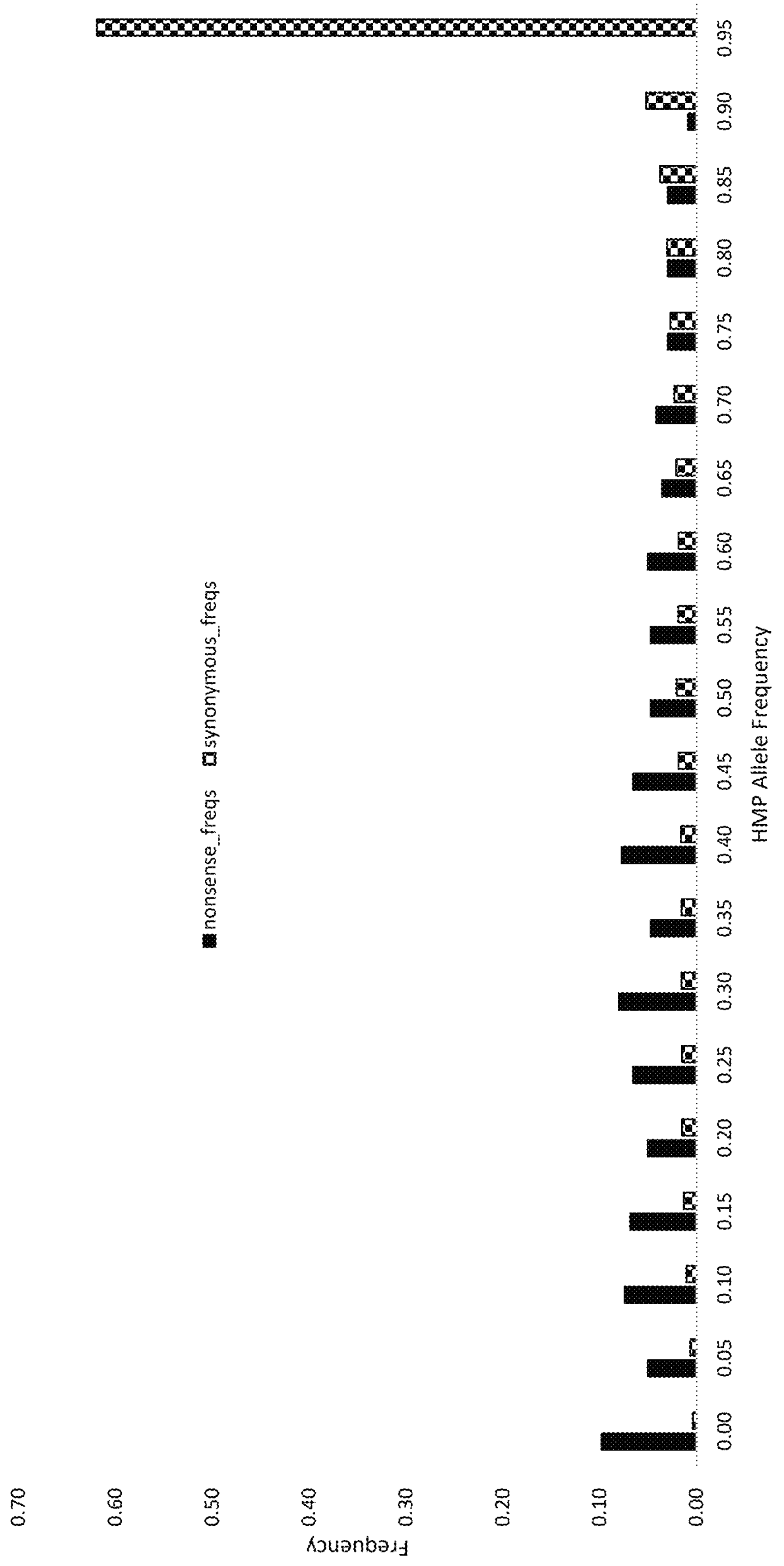
FIG. 4 depicts Target genome allele frequencies of nonsense candidate sites from HapMap3 compared to synonymous alleles from the same target genome.

Discovery of nonsense codons within the target genome relative to the reference set of genes from maize inbred B73 version 4 (Jiao et al 2017) was carried out using the software SNPeff (Cingolani et al. 2012), which annotates polymorphisms with functional information based on their effects on a given set of gene models. An initial set of A/G and T/C polymorphisms between B73 and the target genome was collected and screened for non-redundant bases and *S. pyogenes* PAM motifs, such that the target genome candidate bases were in the A or T configuration and resulted in a stop codon relative to the reference annotation. PAM site, target base redundancy, and overall uniqueness screens were carried out as detailed in example 1. The candidate sites were observed to have even higher enrichment for rare allele than the putatively deleterious missense mutation (FIG. 4), and sites were again prioritized for editing based on their frequency in the population—with rarer mutations assumed to have a higher probability of deleterious impact.

Candidate deleterious mutations may be identified through numerous methods, not limited to the examples described above. Once identified, filtering of these candidate edits to those amenable to base editing follows the general procedure:

1. Screen for PAM sites at the required distance from the target site given the optimal target window properties of the base editor.
2. Screen against redundant target bases within the editing window
3. Screen target sites for sufficient uniqueness within the target genome Given that the technical specifications described above are fulfilled, target identification may encompass myriad processes that specialize on both coding and non-coding portions of the genome. Selection may be based on, for example, biochemical or biophysical properties of the target site, for example but not limited to production of a nonsense codon, interference of a transcription factor binding site, or other factors. Some exemplary, but not limiting, approaches are summarized in Table 1.

TABLE 1

Target Identification Approaches

| Target Set | Prioritization Approach |
|---|---|
| Nonsense coding | Use SNPeff to screen polymorphisms in target compared to annotated reference for mutations amenable to base editing that result in a nonsense substitution within the target |
| Deleterious missense coding | Use SIFT to discover missense polymorphic sites within the target genome that result in a change in amino acid that is predicted not to be tolerated well based on evolutionary conservation |
| Rare alleles | Use the known SNP set to find polymorphisms for which the target genome has a rare allele (e.g. below 0.05 frequency). These may be coding or non-coding. |
| Evolutionarily conserved sites | Use an evolutionary approach insensitive to the coding status of a region (e.g. GERP) (Davydov et al. 2010) to find sites in a multiple nucleotide sequence alignment that have been more conserved than expected under neutrality and have a mutation to a non-conserved allele within the target genome |
| Machine learning prioritized putative regulatory elements | Use a machine learning approach (e.g. deep neural networks) to train a predictor of gene expression based on flanking non-coding sequence. Use trained predictor to identify sites with high functional impact when mutated. Prioritize base editing to target genome alleles with predicted high impact on expression. |

TABLE 1-continued

| Target Identification Approaches | |
|---|---|
| Target Set | Prioritization Approach |
| Locally-adaptive variants | Identify variants with a large signal of differentiation among subpopulations along with a significant association with an environmental variable of interest (e.g. disease prevalence). Target base edits to introduce locally-adapted alleles to target genome |
| Orthology-informed variants of adaptive significance | Identify variants of adaptive significance (e.g. based on selective sweep, GWAS, genetic manipulation) in orthologous genes of other species. Target syntenic site within the target genome to reconstitute the orthologous adaptive site. |
| Stop induction | Screen for sites where knock-out or truncation of a gene is associated with adaptation, and prioritize the induction of nonsense mutations at sites within these genes. |

Example 2: Detection of Sequence Modifications in Base-Edited Plants

In this Example, methods to detect nucleotide polymorphisms resulting from chromosomal target DNA deamination in cells are described. In some aspects, said cell is a plant cell. In one example of a plant cell, a *Zea mays* cell is used.

In cells, the deamination of chromosomal DNA can result in the post-replicative transition to a different nucleotide. By associating deaminases with RNA-guided CRISPR-associated (Cas) proteins, nucleotide polymorphisms (NPs) can be introduced into DNA in a targeted fashion. To monitor these changes, targeted deep sequencing or other equivalent methods were used (Nilsson et al. 1994 and Krishnakumar et al. 2008). Briefly, total genomic DNA was extracted from plant cells by methods known in the art (Gao et al. (2010) *Plant J.* 61:176-187 or Karvelis et al. (2015) *Genome Biol.* 16, 253) and the region surrounding the intended target site was PCR amplified with Phusion® HighFidelity PCR Master Mix (New England Biolabs, M0531L) adding on the sequences necessary for amplicon-specific barcodes and Illumina sequencing using “tailed” primers through two rounds of PCR and deep sequenced on a MiSeq (Illumina). The resulting reads were then examined for the presence of NPs at the expected target site by comparison to control experiments where the small RNA transcriptional cassette was omitted from the transformation.

Example 3: Base-Editing DNA Expression Cassettes

In this Example, methods to optimize polynucleotide cassettes for the expression of CRISPR-associated (Cas) protein(s), guide RNA (gRNA), and deaminase in a cell are described. In some aspects, said cell is a plant cell. In one example of a plant cell, a *Zea mays* cell is used.

In one method, a gene encoding a deaminase (for example but not limited to APOBEC (apolipoprotein B mRNA editing enzyme, catalytic polypeptide-like 1 or ABE (adenine base editing) was plant codon optimized and gene destabilizing features (for example but not limited to MITEs (Miniature Inverted-repeat Transposable Elements) were removed. The resulting open-reading-frame (ORF) was then fused in-frame to the end of a gene also conditioned for expression that encodes Cas protein(s) capable of RNA guided recognition of a double-stranded (ds) DNA target site. In some cases, the cas gene can encode a functional, impaired, or dead nuclease. In other circumstances, additional sequences encoding accessory protein(s) that aid in the conversion of a deaminated nucleotide to a different one were also optimized for expression and attached to the cas gene. In some instances, the cas gene encoded a Cas9, Type I Cascade, Cas-alpha, Type V-U, or Cas14 protein. An intron was also inserted into the resulting cas-deaminase gene to eliminate expression in *E. coli* or *Agrobacterium* prior to plant transformation. Additionally, to facilitate efficient entry into the nucleus, a sequence encoding a nuclear localization signal (NLS) (for example but not limited to a Simian Virus 40 (NLS)) was incorporated into the deaminase, cas, or accessory gene.

The resulting genes engineered for plant cell expression and nuclear localization were next synthesized (for example but not limited to GenScript, Inc.) and operably cloned into a plasmid DNA vector containing an upstream promoter and downstream terminator using standard techniques (for example but not limited to Golden Gate or Gibson assembly). In some instances, the promoter can be a constitutive, spatially or temporally regulated, or inducible.

The deaminase associated Cas complex is directed by small RNAs (referred to herein as guide RNAs) to recognize double-stranded DNA target sites. These guide RNAs comprise a sequence that aids recognition by the Cas protein (referred to as Cas recognition domain) and a sequence that serves to direct dsDNA target recognition by base pairing with one strand of the DNA target site (Cas variable targeting domain). To transcribe small RNAs necessary for directing base-editing in plant cells, a U6 polymerase III promoter and terminator were first isolated from a plant genome and operably fused to the ends of a suitable guide RNA. To promote optimal transcription of the guide RNA from the U6 polymerase III promoter, a G nucleotide is added to the 5' end of the sequence to be transcribed. Polymerase II promoters (for example but not limited to those listed for Cas-deaminase expression) in combination with a ribozyme motif, RNase P and Z cleavage sites, Csy4 (Cas6 or CasE) ribonuclease recognition site, or heterologous RNase can also be used to express the guide RNA. Moreover, the RNA processing provided by these strategies can be harnessed to express multiple guide RNAs from either a single polymerase II or III promoter.

Example 4: Transformation of Plant Optimized Base-Editing Components

In this example, methods for introducing a deaminase linked Cas protein (s) and associated guide polynucleotide(s) into cells are described. In some aspects, said cell is a plant cell. In one example of a plant cell, a *Zea mays* cell is used.

*Zea mays* Transformation

Particle-Mediated Delivery of DNA Expression Cassettes

Particle gun transformation of Hi-Type II 8 to 10-day-old immature maize embryos (IMEs) in the presence of BBM and WUS2 genes was carried-out as described in Svitashev et al. (2015) *Plant Phys.* 169:931-945. Briefly, DNA expression cassettes were co-precipitated onto 0.6 μM (average size) gold particles utilizing TransIT-2020. Next, the DNA coated gold particles were pelleted by centrifugation, washed with absolute ethanol and re-dispersed by sonication. Following sonication, 10 μl of the DNA coated gold particles were loaded onto a macrocarrier and air dried. Next, biolistic transformation was performed using a PDS-1000/He Gun (Bio-Rad) with a 425 pound per square inch rupture disc. Since particle gun transformation can be highly variable, a visual marker DNA expression cassette encoding a yellow fluorescent protein (YFP) was also co-delivered to aid in the selection of evenly transformed IMfEs and each treatment was performed in triplicate. To determine the plant transformation culture conditions optimal for binding or mutational activity, transformed IMEs is incubated at 28° C. for 48 hours, or at a range of temperatures lower or higher than 28° C. to establish the temperature optimum for base editing.

Particle-Mediated Ribonucleoprotein Delivery

Cas9-deaminase and associated guide polynucleotide(s) ribonucleoprotein (RNP) complex(es) can be delivered by particle gun transformation as described in Svitashev, S. et al. (2016) Nat. Commun. 7:13274. Briefly, RNPs (and optionally DNA expression) are precipitated onto 0.6 mm (average diameter) gold particles (Bio-Rad) using a water soluble cationic lipid TransIT-2020 (Mirus) as follows: 50 ml of gold particles (water suspension of 10 mg/ml) and 2 ml of TransIT-2020 water solution are added to the premixed RNPs (and optionally DNA expression vectors), mixed gently, and incubated on ice for 10 min. RNP/DNA-coated gold particles are then pelleted in a microfuge at 8,000g for 30 s and supernatant is removed. The pellet is then resuspended in 50 ml of sterile water by brief sonication. Immediately after sonication, coated gold particles are loaded onto a microcarrier (10 ml each) and allowed to air dry. Immature maize embryos, 8-10 days after pollination, are then bombarded using a PDS-1000/He Gun (Bio-Rad) with a rupture pressure of 425 pounds per inch square. Post-bombardment culture, selection, and plant regeneration are performed using methods known in the art.

*Agrobacterium*-Mediated Transformation

*Agrobacterium*-mediated transformation is performed essentially as described in Djukanovic et al. (2006) *Plant Biotech J.* 4:345-57. Briefly, 10-12 day old immature embryos (0.8-2.5 mm in size) are dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium is replaced with 1 ml *Agrobacterium* at a concentration of 0.35-0.45 OD550. Maize embryos are incubated with *Agrobacterium* for 5 min at room temperature, then the mixture is poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos are incubated axis down, in the dark for 3 days at 20° C., then incubated 4 days in the dark at 28° C. or at a range of temperatures lower or higher than 28° C. to establish the temperature optimum for base editing. After approximately 7 days, they may be harvested for DNA extraction.

In another variation for stable transformation, the embryos are then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos are subcultured every three weeks until transgenic events are identified. Somatic embryogenesis is induced by transferring a small amount of tissue onto regeneration medium (4.3 g/L MS salts (Gibco 11117), 5.0 ml/L MS Vitamins Stock Solution, 100 mg/L myo-inositol, 0.1 uM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots are transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets are moved into glass tubes containing the same medium and grown until they were sampled and/or transplanted into soil.

Example 5: Optimizing Base-Editing for Plants

Figures 6A, 6B:
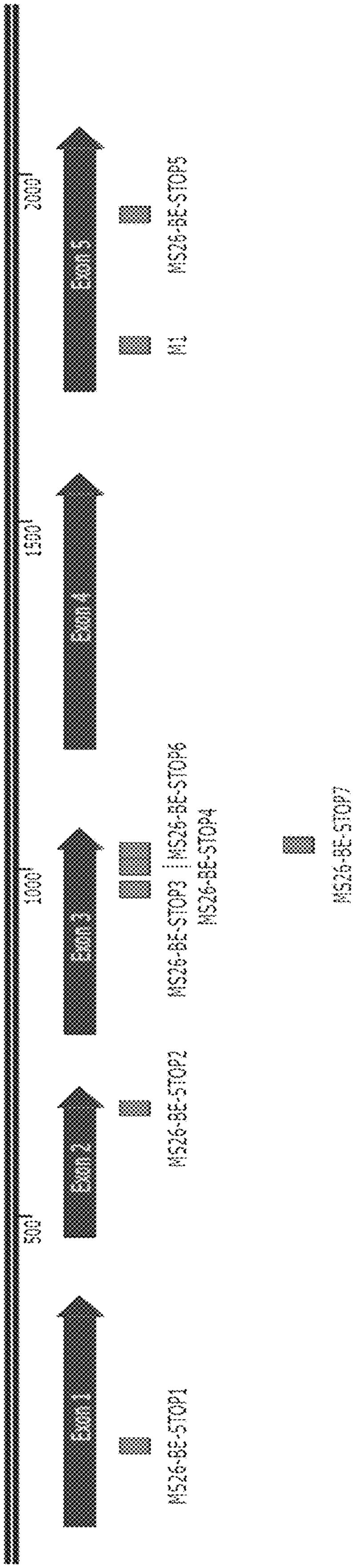
FIG. 6A depicts exons of the MS26 locus in maize.
FIG. 6B shows the cytosine nucleobases at the MS26 locus that were targeted for base editing.

This Example describes methods to optimize the recovery of plant cells containing a targeted nucleotide polymorphism(s) resulting from base-editing. In some aspects, said cell is a plant cell. In one example of a plant cell, a *Zea mays* cell is used to edit the nucleotide composition of chromosomal DNA targets In one method, DNA targets are selected based on the context of the nucleotides adjacent to the nucleotide to be deaminated. Here, the nucleotides adjacent to the nucleotide targeted for deamination are correlated with editing efficiency. As an example, different exons of the male sterile 26 (MS26) gene were selected and the nucleotide context surrounding the target cytosine nucleotide were noted (FIGS. 6A and B). It was observed that the nucleotide preceding the target cytosine influenced the rate of *Streptococcus pyogenes* (Sp) Cas9-APOBEC (apolipoprotein B mRNA editing enzyme, catalytic polypeptide-like 1) deamination and transition from cytosine to thymine. These findings also extended to plants regenerated from our experiments. Here, while the conversion of cytosine to thymine was detected at both MS26 BE-STOP1 and 4 sites, the frequency of editing was drastically improved at the MS26 BE-STOP1 target when the preceding nucleotide was a thymine or cytosine (FIG. 6B). For the MS26-BE-STOP1 locus, the actual recovery from approximately 380 plants was 71%, with the majority (43%) being homozygous for the intended edit (and less than 1% indels). For the MS26-BE-STOP4 locus, the actual recovery was 16% with only 1% being homozygous for the intended edit (and less than 1% indels). In all, our findings show that the bases surrounding the nucleotide targeted for deamination play a critical role in optimal base-editing.

Example 6: Design, Optimization, and Delivery of Guide RNAs for Multiplex Editing This Example describes the design, optimization, and delivery of CRISPR-associated guide RNA expression cassettes to modify multiple target polynucleotides in the genome of a cell. In some aspects, said cell is a plant cell. In one example of a plant cell, a *Zea mays* cell is used.

A guide RNA (gRNA) capable of directing a CRISPR-associated (Cas) protein or complex to recognize a chromosomal DNA target site are comprised of two RNA polynucleotides, a CRISPR RNA (crRNA) and optionally a trans-activating RNA (tracrRNA). In the case of a tracrRNA, the crRNA and tracrRNA can be also linked into a single guide RNA (sgRNA) transcript. To enable expression in cells, gRNA expression cassettes are constructed and contain a promoter (polymerase II or III), the sequence encoding the guide RNA, and a terminator region. For *Zea mays*, a U6 polymerase III promoter, sequence encoding a single guide RNA (sgRNA) engineered from *Streptococcus pyogenes* (Sp) Cas9 (~97 bp), and terminator (8 bp, TTTTTTTT) can be utilized (Svitashev et al. 2015).

Two methods, Particle Gun and *Agrobacterium*, are typically used to deliver DNA expression constructs into plant cells. Both methods limit the size and number of different expression constructs that can be delivered. Therefore, approaches to maximize the delivery of gRNA expression cassettes are desirable and would enable large-scale multi-site chromosomal editing.

In one method, the promoter of the gRNA expression cassette can be truncated. This approach can be used to approximate the minimal promoter length that facilitates robust gRNA expression and thus maximize the amount of sequence space. Here, the *Zea mays* U6 promoter, previously used to express a sgRNA for SpCas9 was systematically truncated. Promoter lengths of 500 bp, 250 bp, and 150 bp performed equivalently to the one described previously (1000 bp in Svitashev et al., 2015). Taken together, this showed that a *Zea mays* U6 promoter as small as 150 bp supports robust sgRNA expression.

In another method, a gRNA expression cassette can be delivered as a linear fragment. In this case, extra DNA from a plasmid vector (e.g. plasmid DNA resistance marker and origin of replication) is removed allowing more copies of the expression cassette (per DNA weight) to be loaded onto particles (e.g. gold) for biolistic delivery. This approach permitted equivalent sgRNA expression (as measured by Cas9-sgRNA target cleavage and repair) from approximately 10-fold less DNA. Altogether, increasing the capacity on the particle by approximately 10-fold.

In another method, multiple sgRNA expression cassettes can be delivered by *Agrobacterium* transformation. In this approach, multiple sgRNA expression cassettes comprised of a minimal promoter, sequence encoding the sgRNA, and terminator can be constructed in a modular fashion using Golden Gate assembly. Cassettes can be first constructed into "mini-chunks" and then combined into larger units, "mega- and giga-chunks", using Type IIS restriction enzymes. To reduce the potential for recombination between similar regions of the expression cassettes (promoter and sequence encoding the sgRNA), a sequence diverse collection of U6 promoters (SEQ ID NOs:17-22) and sgRNA sequences (SEQ ID NOs:23-26) can be used. Additionally, *E. coli* and *Agrobacterium* strains with altered DNA repair pathways that reduce the propensity for recombination between similar DNA sequences can also be utilized.

In another method, multiple T-DNAs encoding different collections of sgRNAs can be co-delivered into a single plant cell as described in the art (Li et al. (2009) *Plant Cell Tiss Organ Cult.* 97:225-235 and Liu et al., (2020) *The Plant Cell.* 32:1397-1413).

Example 7: Evaluation of Multiplex Base Editing in Plants and Use of Data for Algorithm Refinement Allele selection for multiplex locus modification is performed according to any of the methods described herein. Guide RNAs are designed to target a plurality of identified loci, and transformed into at least one cell of the recipient plant, along with a Cas endonuclease.

In some aspects, individual single guide RNAs (linking both the tracrRNA and crRNA components) are provided. In some aspects, specific crRNAs are introduced into the target cell(s), along with a static tracrRNA and Cas endonuclease.

Any one or more of the components may be introduced by particle bombardment or Rhizobiales-mediated transformation (e.g., *Agrobacterium* or Ochrobactrum).

In one example, a plurality of guides are introduced on a single vector that is introduced into one *Agrobacterium* strain. Multiple different *Agrobacterium* strains, each comprising a different set of a plurality of guides, are transformed into the host cell.

In one example, a plurality of guides are coated onto a microparticle for bombardment, for example on linear constructs or plasmids.

In one example, a CRISPR-type array of spacers and repeats are synthesized, wherein each "repeat" sequence comprises the crRNA portion of a guide RNA.

In one example, a vector is constructed with a plurality of guide RNAs (sgRNA or crRNA), separated by a cleavage recognition sequence, so that the individual components are released into the host cell.

Plants will comprise a mixture of beneficial edits (multiple edits per plant, ranging from 2 to 5 to 10 to 100 to 1000 to greater than 1000). A TO plant comprising a plurality of edits may be crossed with other plants (such as another TO plant, or selfed) that comprises overlapping or different sets of edits that are potentially beneficial. T1 offspring of the cross can be selected for any one or more desired characteristic(s). Other types of crosses, backcrosses, outcrosses, etc. are contemplated for any desired purpose (see FIG. 2 for some non-limiting examples).

The presence of edits may be assessed with markerplex technology. Phenotype(s) of the F1 offspring are assessed for differential phenotypes, for example those related to reproductive traits, seed production, yield, plant health, and vigor. Not all edits are predicted to occur with the same frequency or with the same effects. Assuming that each individual edit results in a small effect, cumulative/added effects from multiple edits would be expected to result in a normal distribution.

A prediction algorithm was developed to simulate the results of different numbers of edits, for alleles with varying effect size.

In general, the simulation comprised the following. A number of loci sere selected for editing. A distribution was chosen for the effect of the edits (for example, a gamma distribution, and assuming that the effects acted additively; however, the assumptions may be variable according to the user's selection). A distribution for the probability of successful edits per TO plant was chosen (for example, a beta distribution, or a mixture of beta distributions for explicitly modeling the effect of base context on editing frequency). It was assumed that the editing frequency was independent of the effect size. The measured phenotype was then simulated for each of a specified number of inbred line, sampling the edits according to the assumptions, and the effects of those edits were added up, adding normally-distributed Gaussian noise (assuming a variance of 1), such that the effect sizes were interpreted in terms of a percentage of expected environmental noise. Other types of noise may be introduced instead of or in addition to, such as non-Gaussian nose (e.g., binary noise for a trait scored as susceptible or non-susceptible. The distributions of the phenotypes between wild type inbreds (simulated to have the environmental noise) and the edited inbreds (simulated to have environmental noise+edit effects) were compared. Allele effects were estimated using a Bayesian Ridge regression (but other methods could be used). The simulation was also run to incorporate some number of negative editing effects, the introduction of random deleterious effects due to transformation, and explicit crossing schema that followed desired clean-up or recombination (intercrossing) steps.

In one example, the edited alleles were evaluated in either the selfed state or backcrossed to the WT (wild type) in an F1 during evaluation, and that edit effects are distributed according to a gamma distribution. Gaussian noise was added to this for the final phenotypes. Each edit also had some success rate of being made, distributed according to a beta distribution across the loci. Edits were also made in groups (e.g. if individual cassettes were made), such that each edit occurred in some number of groups with random allocation among the groups. The distribution of effects, the heritability within the edited group, and the expected distributions of phenotypes in the edited population were compared to the WT.

Figure 5A:
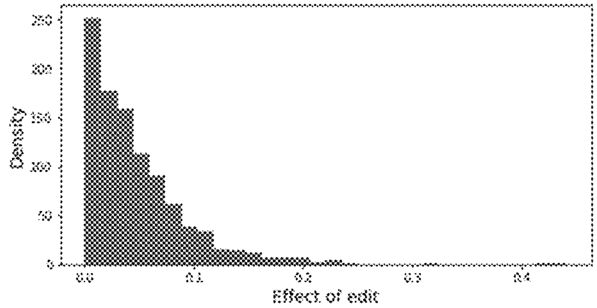
FIG. 5A is a frequency distribution of allele effects for one predictive model of editing outcomes, with an average effect size equal to 5% of the environmental standard deviation.
Figure 5B:
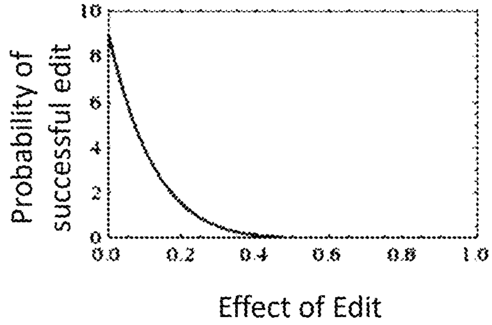
FIG. 5B is one example distribution of probability of successful edits.
Figure 5C:
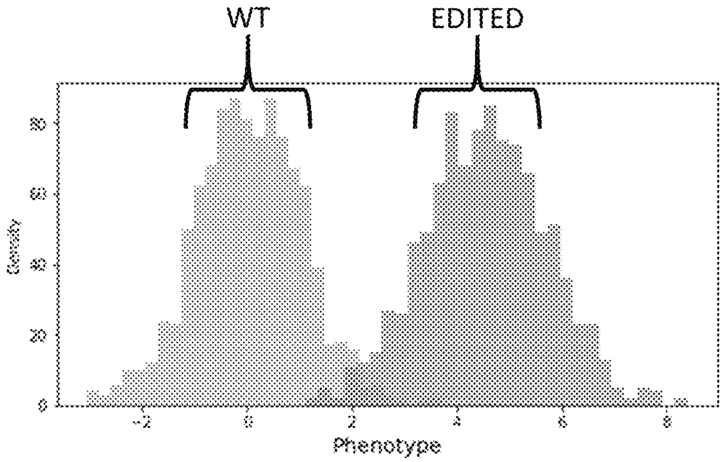
FIG. 5C shows the predicted results of 1000 edits based on the parameters of 5A and 5B.
Figure 5D:
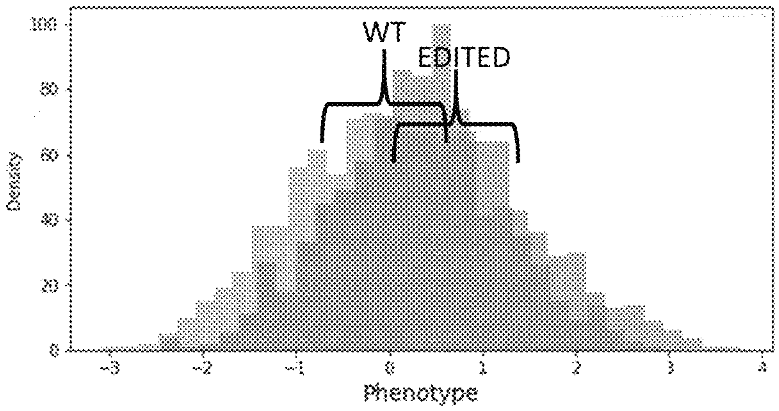
FIG. 5D shows the predicted results of 100 edits based on the parameters of 5A and 5B.
Figure 5E:
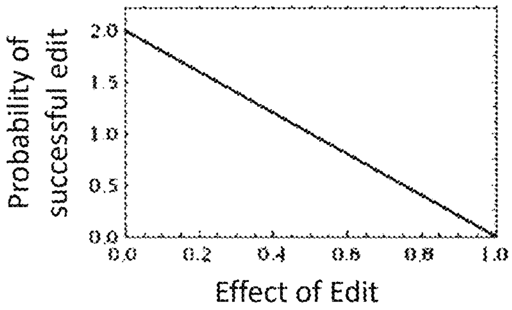
FIG. 5E is one example distribution of probability of successful edits.
Figure 5F:
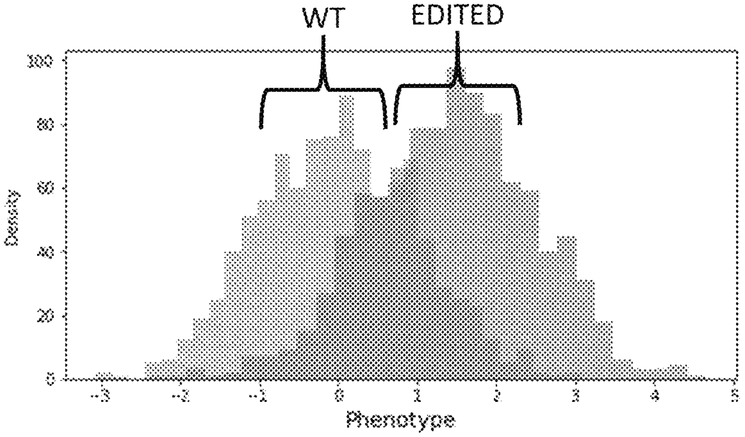
FIG. 5F shows the predicted results of 100 edits based on the parameters of 5E.
Figure 5G:
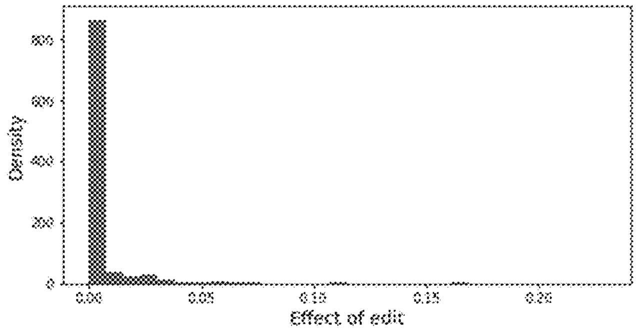
FIG. 5G is a frequency distribution of allele effects for one predictive model of editing outcomes, with an average effect size equal to 0.5% of the environmental standard deviation.
Figure 5H:
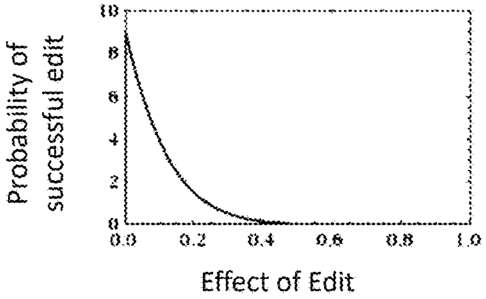
FIG. 5H is one example distribution of probability of successful edits.
Figure 5I:
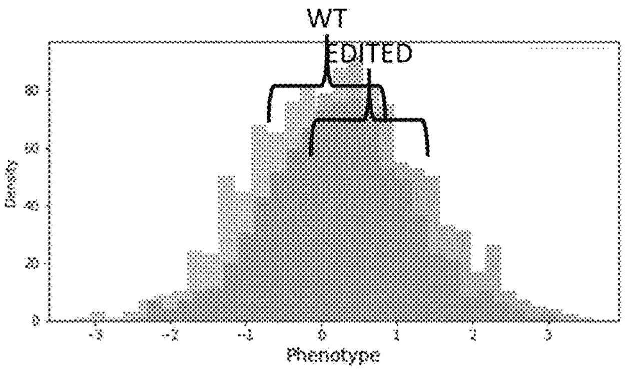
FIG. 5I shows the predicted results of 1000 edits based on the parameters of 5H and 5G.
Figure 5J:
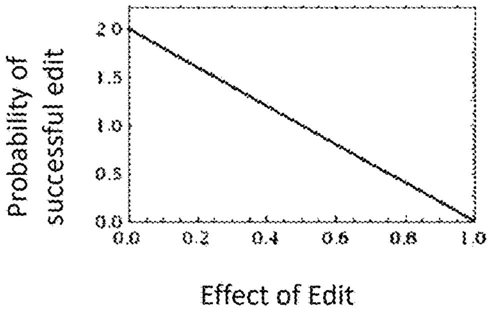
FIG. 5J is one example distribution of probability of successful edits.
Figure 5K:
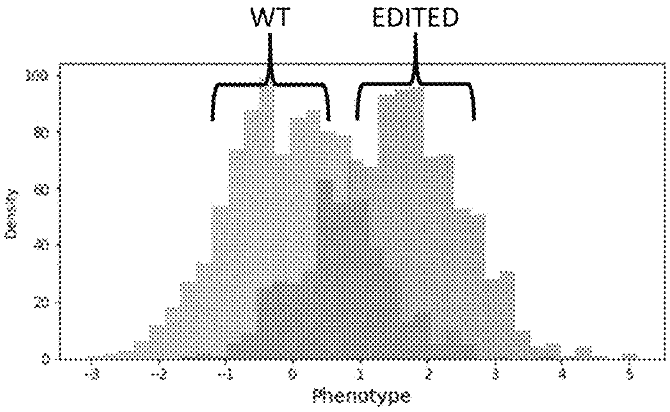
FIG. 5K shows the predicted results of 1000 edits based on the parameters of 5J and 5G.

Each allele was assigned a probability of effect and a was curve obtained (x axis is the probability that any given edit is made, y-axis is how common the result is, for the cumulative allele edits). Initial assumptions included the presence of hundreds of nonsense mutations, thousands of putative deleterious missense mutations, and thousands of slightly deleterious regulatory region variants. An initial assumption of an average effect size of 5% (FIG. 5A) was used. For the probability of successful edits model shown in FIG. 5B, 1000 edits resulted in a predicted distribution of the WT phenotype that was distinct from the predicted distribution of the edited phenotype (FIG. 5C). However, 100 edits resulted in a predicted distribution of the WT phenotype that more overlapping with the predicted distribution of the edited phenotype (FIG. 5D). Changing the probability distribution to allow for increased rates of highly edited sites (FIG. 5E) for 100 edits resulted in a more distinct separation between the edited and wild-type populations (FIG. 5F). Shifting the average effect size to 0.5% (FIG. 5G) for 1000 edits results in a highly overlapping phenotype dataset for the probability of success model shown in FIG. 5H, while changing to the higher efficiency distribution (FIG. 5I) results in a more separation between the edited and wild-type populations (FIG. 5J). Marker analysis in the F1 generation allows an assessment of frequency of the edits independent of variations due to the transformation process that aren't necessarily associated with the edits themselves.

Allele modification results are inputted back into the original algorithm for method refinement.

Figure 2:
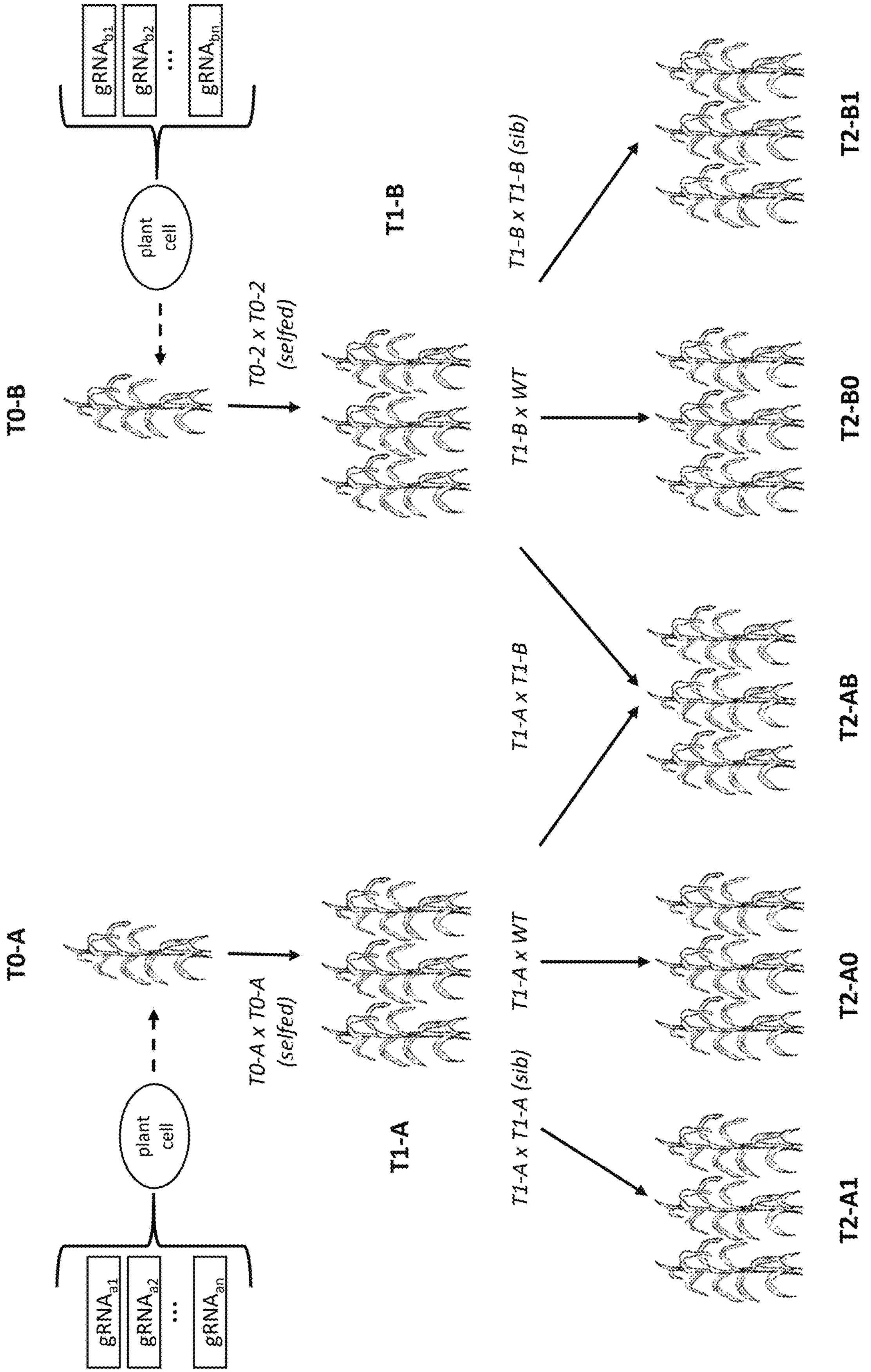
FIG. 2 depicts some examples of creating edited plant lines and subsequent generations for any desired use.

Example 8: Uses of Multiplexed Edited Plant Lines in Plant Breeding Programs T0 plants are generated as described above. As shown in FIG. 1, multiplex marker analysis can be used on a population of transformed cells or organisms, or on subsequent progeny generation(s), to refine the data for the input model. FIG. 2 shows some examples of generating additional generations of plants with multiple edits.

In this example, potential impacts of the methods and compositions described above are presented. Identification of one or more principal component (PC) edits is possible, wherein the PC edits may be used for optimization of other plant lines. Immediate phenotypic gains may be realized from a single generation. Accelerated breeding may be accomplished: lack of recombination is less of a barrier, and parental traits may be fixed in an inbred for less constrained advancement. The T1 generation created by selfing or inter-crossing two TO plants may provide the benefits of hybrid vigor in an inbred line, as the potentially deleterious alleles would be ameliorated without an outcross, while avoiding inbreeding depression. Improved predictions of what constitutes a deleterious allele may be obtained, and biologically-informed whole-genome predictions may become possible.

Higher-powered multiplexed base editing may be accomplished by crossing two plants that each have a population of edits, for example one plant with 1000 edits may be crossed with another plant with 1000 different edits, to create a progeny plant with more edits than either of the parents. Various types of selfing, backcrossing to WT, outcrossing to other edited plants, or other types of breeding, can produce plants with a selected genotype (or phenotype) with a fixed particular allele edit in the germline.

Example 9: Characterization and Optimization of Multiplexed Base Editing in Plants Any base editing complex, such as a base editing agent associated with an RNA-guided protein, may be used to target and bind to a desired locus in the genome of an organism and chemically modify one or more components of a target polynucleotide. Biochemical and biophysical properties of the editing complex are assessed at different temperatures, salt concentrations, buffer compositions, pressures, incubation times, and other conditions. The base editing complex displays a preference for a particular optimal condition, such as a temperature.

Plant cells were exposed to elevated temperatures. Plant cells are ectothermic and protocols for plant transformation suggest that temperatures be carefully maintained around 28° C. At these temperatures, base deamination and conversion and a cognate guide RNA failed to occur, and that activity was only recovered when cells were incubated at 37° C.

A polynucleotide encoding one or more components of the base editing complex may be operably linked to an inducible promoter, for controlled expression and activity.

Example 10: Uses of Multiplexed Edited Plant Lines in Developing a Training Dataset for Plant Breeding T0 plants are generated as described above. As shown in FIG. 1, multiplex marker analysis can be used on a population of transformed cells or organisms, or on subsequent progeny generation(s), to refine the data for the input model. FIG. 2 shows some examples of generating additional generations of plants with multiple edits.

In this example, potential impacts of the methods and compositions described above are presented. Identification of one or more principal component (PC) edits is possible, wherein the PC edits may be used for optimization of other plant lines. Immediate phenotypic gains may be realized from a single generation. Accelerated breeding may be accomplished: lack of recombination is less of a barrier, and parental traits may be fixed in an inbred for less constrained advancement.

In this Example, the edited plants are generated as described above in Example 8, but the edited plants themselves do not become part of the breeding program, but provide estimation datasets for predicting crosses and selecting non-edited lines in a parallel breeding program where the plants have not gone through an editing process. For example, a population of genome edited may plants and subsequent phenotypic and/or genotypic analysis can provide data to an agriculturally intelligent computer capable of machine learning. The machine learning algorithm can be trained to predict favorable and/or non-favorable genotypes and/or phenotypes.

We claim:

1. A method of base editing in a plant cell, the method comprising:

selecting a plurality of polymorphic sites in the genome of the plant, wherein selecting the plurality of polymorphic sites comprises:

(a) calculating a selection score for each polymorphic site of the plurality of polymorphic sites, wherein the selection score is based on evolutionary conservation of each polymorphic site; and (b) selecting polymorphic sites with selection scores that meet a user-defined criterion and comprise a nucleotide sequence capable of being modified by base editing; and introducing into the plant cell a base editing agent, wherein the base editing agent alters a nucleobase in one or more selected polymorphic sites.

2. A method of altering a characteristic of a plant, the method comprising:

(a) selecting a plurality of target sites in a plant cell, wherein the plurality of target sites each comprise a single nucleotide polymorphism, wherein selecting the plurality of target sites comprises:

calculating a selection score for a single nucleotide polymorphism within each of the plurality of target sites, wherein the selection score is based on evolutionary conservation of the single nucleotide polymorphism; and selecting the plurality of target sites, wherein each selected target site comprises a single nucleotide polymorphism with a selection score that meets a user-defined criterion, wherein the single nucleotide polymorphism is capable of being modified by base editing;

(b) introducing into the plant cell a composition comprising:

(i) a plurality of different guide RNAs that each share sufficient homology with a different selected target site;

(ii) an RNA-guided protein that forms a complex with a guide RNA of the plurality of different guide RNAs, and (iii) a base editing agent;

wherein the composition alters the single nucleotide polymorphism within one or more selected target sites;

(c) regenerating a plant from the plant cell; and (d) assessing the plant for the presence of an altered characteristic, as compared to an isoline plant that did not have the composition introduced.

3. The method of claim 2, further comprising crossing the plant with a second plant to obtain a third plant.

4. The method of claim 2, further comprising self-crossing the plant to obtain progeny.

5. The method of claim 3, wherein the second plant is a wild type plant.

6. The method of claim 3, wherein the second plant is a sibling plant.

7. The method of claim 3, wherein the second plant comprises a plurality of edited nucleobases.

8. The method of claim 3, wherein the third plant is crossed with a fourth plant.

9. The method of claim 8, wherein the fourth plant is a plant obtained from step (c).

10. The method of claim 8, wherein the fourth plant is a wild type plant.

11. The method of claim 8, wherein the fourth plant is a sibling plant.

12. The method of claim 8, wherein the fourth plant comprises a plurality of edited nucleobases.

13. The method of claim 8, wherein the fourth plant is a parental plant.

14. A method of creating a population of plants with an altered characteristic, the method comprising: crossing a plant obtained from step (c) of claim 2 with a second plant to obtain a population of plants.

15. The method of claim 1, wherein the one or more selected polymorphic sites is at least 5.

16. The method of claim 1, wherein the nucleobase in the one or more selected polymorphic sites is cytosine.

17. The method of claim 1, wherein the nucleobase in the one or more selected polymorphic sites is adenine.

18. The method of claim 1, wherein the base editing agent is a composition comprising:

(i) an RNA-guided protein;

(ii) a plurality of different guide RNAs that each share sufficient homology with a different selected polymorphic site; and (iii) a deaminase.

19. The method of claim 18, wherein the base editing agent further comprises:

(iv) a uracil glycosylase inhibitor.

20. The method of claim 18, wherein the deaminase is a cytosine deaminase.

21. The method of claim 18, wherein the deaminase is an adenine deaminase.

22. The method of claim 18, wherein the RNA-guided protein is a nickase.

23. The method of claim 22, wherein the nickase is a Cas nickase (nCas).

24. The method of claim 18, wherein the RNA-guided protein is a catalytically inactive endonuclease.

25. The method of claim 24, wherein the catalytically inactive endonuclease is a deactivated Cas endonuclease (dCas).

26. The method of claim 2, wherein the composition further comprises:

(iv) a uracil glycosylase inhibitor.

27. The method of claim 2, wherein the base editing agent is a deaminase.

28. The method of claim 27, wherein the deaminase is a cytosine deaminase.

29. The method of claim 27, wherein the deaminase is an adenine deaminase.

30. The method of claim 2, wherein the RNA-guided protein is a nickase.

31. The method of claim 30, wherein the nickase is a Cas nickase (nCas).

32. The method of claim 2, wherein the RNA-guided protein is a catalytically inactive endonuclease.

33. The method of claim 32, wherein the catalytically inactive endonuclease is a deactivated Cas endonuclease (dCas).

34. The method of claim 2, wherein the one or more selected target sites is at least 5.

35. The method of claim 2, wherein the single nucleotide polymorphism is cytosine.

36. The method of claim 1, wherein the single nucleotide polymorphism is adenine.

37. The method of claim 1, wherein the one or more selected polymorphic sites constitute a rare allele.

38. The method of claim 2, wherein the one or more selected target sites constitute a rare allele.

39. The method of claim 1, wherein the one or more selected polymorphic sites comprises a deleterious missense mutation.

40. The method of claim 2, wherein the one or more selected target sites comprises a deleterious missense mutation.

41. The method of claim 1, wherein the one or more selected polymorphic sites are in a coding region of the plant cell genome.

42. The method of claim 2, wherein the one or more selected target sites are in a coding region of the plant cell genome.

43. The method of claim 1, wherein the one or more selected polymorphic sites are in a noncoding region of the plant cell genome.

44. The method of claim 2, wherein the one or more selected target sites are in a noncoding region of the plant cell genome.

* * * * *

SEQUENCE LISTING

```
<160> NUMBER OF SEQ ID NOS: 26

<210> SEQ ID NO 1
<211> LENGTH: 167
<212> TYPE: PRT
<213> ORGANISM: Escherichia coli

<400> SEQUENCE: 1

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165


<210> SEQ ID NO 2
<211> LENGTH: 168
<212> TYPE: PRT
<213> ORGANISM: Enterobacteriaceae bacterium strain FGI 57

<400> SEQUENCE: 2

Met Ser Asp Asn Glu Phe Asn His Glu Tyr Trp Met Arg His Ala Leu
1               5                   10                  15

Thr Leu Ala Gln Arg Ala Trp Asp Glu Gly Glu Val Pro Val Gly Ala
            20                  25                  30

Val Leu Val Leu Asp Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Met Val Leu Gln Asn Tyr Arg Leu Ile Asn Ala Thr Leu
65                  70                  75                  80

Tyr Val Thr Leu Glu Pro Cys Val Met Cys Ala Gly Ala Met Val His
                85                  90                  95
```

```
Ser Arg Ile Gly His Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Val Thr Glu Gly Val Leu Arg Glu Gln Cys Ala Gly Met
    130                 135                 140

Leu Ser Asp Phe Phe Arg Glu Arg Arg Glu Gln Ile Lys Ala Leu Arg
145                 150                 155                 160

Lys Ala Gln Lys Ala Glu Asn Gln
                165


<210> SEQ ID NO 3
<211> LENGTH: 167
<212> TYPE: PRT
<213> ORGANISM: Kluyvera georgiana

<400> SEQUENCE: 3

Met Ser Asp Ile Glu Gln Asn His Glu Tyr Trp Met Arg His Ala Leu
1               5                   10                  15

Ala Leu Ala Arg Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Val Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Gly Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Ala Asp Glu Cys Ser Ala Met
    130                 135                 140

Leu Ser Asp Phe Phe Arg His Arg Arg Gln Gln Gln Lys Ala Leu Lys
145                 150                 155                 160

Gln Ser Leu Lys Asn Ser Leu
                165


<210> SEQ ID NO 4
<211> LENGTH: 169
<212> TYPE: PRT
<213> ORGANISM: Klebsiella pneumoniae (30)

<400> SEQUENCE: 4

Met Ser Asp Leu Glu Leu Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80
```

```
Tyr Val Thr Leu Glu Pro Cys Val Met Cys Ala Gly Ala Met Val His
                85                  90                  95

Ser Arg Ile Ala Arg Leu Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Ser Glu Gly Val Leu Ala Glu Ser Cys Ser Ala Met
    130                 135                 140

Leu Ser Asp Phe Phe Arg Trp Arg Arg Glu Glu Lys Lys Ala Gln Lys
145                 150                 155                 160

Lys Ala Arg Glu Gln Thr Gly Glu Ser
                165


<210> SEQ ID NO 5
<211> LENGTH: 167
<212> TYPE: PRT
<213> ORGANISM: Klebsiella aerogenes (27)

<400> SEQUENCE: 5

Met Ser Asp His Glu Phe Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Ile Leu Ala Glu Ser Cys Ser Ala Met
    130                 135                 140

Leu Ser Asp Phe Phe Arg Trp Arg Arg Glu Glu Lys Lys Ala Leu Arg
145                 150                 155                 160

Lys Ala Arg Gln Glu Glu Gly
                165


<210> SEQ ID NO 6
<211> LENGTH: 166
<212> TYPE: PRT
<213> ORGANISM: Kluyvera ascorbata ATCC 33433

<400> SEQUENCE: 6

Met Ser Asp Ile Glu Leu Asn His Glu Tyr Trp Met Arg His Ala Leu
1               5                   10                  15

Val Leu Ala Gln Arg Ala Trp Asp Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60
```

-continued

```
Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Gly Arg Ile Gly Asn Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Ala Glu Glu Cys Ser Ala Met
    130                 135                 140

Leu Ser Asp Phe Phe Arg His Arg Arg Gln Gln Gln Lys Ala Leu Arg
145                 150                 155                 160

Gln Ala Glu Lys Gly Ser
                165


<210> SEQ ID NO 7
<211> LENGTH: 168
<212> TYPE: PRT
<213> ORGANISM: Raoultella sp. (18)

<400> SEQUENCE: 7

Met Ser Asp His Glu Arg Asn Asp Glu Tyr Trp Met Arg His Ala Leu
1               5                   10                  15

Thr Leu Ala Lys Arg Ala Trp Glu Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Ile Arg
    50                  55                  60

Gln Gly Gly Leu Val Leu Gln Asn Tyr Arg Leu Ile Asp Ala Thr Leu
65                  70                  75                  80

Tyr Val Thr Leu Glu Pro Cys Val Met Cys Ala Gly Ala Met Val His
                85                  90                  95

Ser Arg Ile Ser Arg Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Ala Glu Gly Val Leu Ala Glu Ser Cys Ser Ala Met
    130                 135                 140

Leu Ser Asp Phe Phe Arg Trp Arg Arg Glu Glu Lys Lys Ala Leu Lys
145                 150                 155                 160

Lys Ala Arg Gln Ala Asp Glu Ser
                165


<210> SEQ ID NO 8
<211> LENGTH: 167
<212> TYPE: PRT
<213> ORGANISM: Klebsiella sp. RIT-PI-d

<400> SEQUENCE: 8

Met Ser Asp His Glu Leu Asn His Glu His Trp Met Arg His Ala Leu
1               5                   10                  15

Thr Leu Ala Gln Arg Ala Trp Asp Glu Gly Glu Val Pro Val Gly Ala
            20                  25                  30

Val Leu Val His Glu Asn Arg Val Ile Gly Glu Gly Trp Asn Arg Pro
        35                  40                  45
```

Ile Gly Arg His Asp Pro Thr Ala His Ala Glu Ile Met Ala Leu Arg
50 55 60

Gln Gly Gly Leu Val Leu Gln Asn Tyr Arg Leu Ile Asp Thr Thr Leu
65 70 75 80

Tyr Val Thr Leu Glu Pro Cys Val Met Cys Ala Gly Ala Met Val His
85 90 95

Ser Arg Ile Gly Gln Leu Val Phe Gly Ala Arg Asp Ala Lys Thr Gly
100 105 110

Ala Ala Gly Ser Leu Ile Asp Ile Leu His His Pro Gly Met Asn His
115 120 125

Arg Val Glu Phe Thr Glu Gly Val Leu Lys Asp Thr Cys Ala Thr Leu
130 135 140

Leu Ser Glu Phe Phe Arg His Arg Arg Gln Val Lys Lys Ala Leu Arg
145 150 155 160

Gln Ala Glu Lys Asp Pro Arg
165

<210> SEQ ID NO 9
<211> LENGTH: 179
<212> TYPE: PRT
<213> ORGANISM: Pseudocitrobacter faecalis

<400> SEQUENCE: 9

Met Arg Pro Asp Leu Ser Ser Gly Val Pro Ala Leu Ser Asp Asn Glu
1 5 10 15

Phe Asn His Glu Tyr Trp Met Arg His Ala Leu Thr Leu Ala Gln Arg
20 25 30

Ala Trp Asp Glu Gly Glu Val Pro Val Gly Ala Val Leu Val Leu Asp
35 40 45

Asn Gln Val Ile Gly Glu Gly Trp Asn Arg Pro Ile Gly Arg His Asp
50 55 60

Pro Thr Ala His Ala Glu Ile Met Ala Leu Arg Gln Gly Gly Met Val
65 70 75 80

Leu Gln Asn Tyr Arg Leu Ile Asn Ala Thr Leu Tyr Val Thr Leu Glu
85 90 95

Pro Cys Val Met Cys Ala Gly Ala Met Val His Ser Arg Ile Gly Arg
100 105 110

Val Val Phe Gly Ala Arg Asp Ala Lys Thr Gly Ala Ala Gly Ser Leu
115 120 125

Met Asp Val Leu His His Pro Gly Met Asn His Arg Val Glu Val Thr
130 135 140

Glu Gly Ile Leu Arg Asp Gln Cys Ala Ser Met Leu Ser Asp Phe Phe
145 150 155 160

Arg Glu Arg Arg Glu Gln Ile Lys Ala Leu Arg Lys Ala Gln Lys Ala
165 170 175

Gly Asn Gln

<210> SEQ ID NO 10
<211> LENGTH: 168
<212> TYPE: PRT
<213> ORGANISM: Enterobacter cloacae (15)

<400> SEQUENCE: 10

Met Ser Ile Pro Glu Tyr Asn His Glu Tyr Trp Met Arg His Ala Leu
1 5 10 15

-continued

```
Thr Leu Ala Gln Arg Ala Trp Asp Glu Gly Glu Val Pro Val Gly Ala
            20                  25                  30

Val Leu Val His Asn Asn Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Leu Asp Thr Thr Leu
65                  70                  75                  80

Tyr Val Thr Leu Glu Pro Cys Val Met Cys Ser Gly Ala Met Val His
                85                  90                  95

Ser Arg Ile Gly Thr Leu Val Phe Gly Ala Arg Asp Glu Lys Thr Gly
            100                 105                 110

Ala Ala Gly Ser Leu Met Asp Val Leu Gly His Pro Gly Met Asn His
        115                 120                 125

Gln Val Lys Thr Ile Gly Gly Val Leu Ala Pro Glu Cys Ser Gly Leu
    130                 135                 140

Leu Ser Asp Phe Phe Arg Met Arg Arg Gln Gln Lys Lys Gln Gln Lys
145                 150                 155                 160

Ala Glu Leu Lys Leu Leu Gly Asp
                165


<210> SEQ ID NO 11
<211> LENGTH: 164
<212> TYPE: PRT
<213> ORGANISM: Citrobacter youngae

<400> SEQUENCE: 11

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Arg Trp Val Arg
            20                  25                  30

Tyr Trp Tyr Ile Thr Thr Ala Phe Gly Glu Gly Trp Asn Arg Pro Ile
        35                  40                  45

Gly His His Asp Pro Thr Ala His Ala Glu Ile Met Ala Leu Arg Gln
    50                  55                  60

Gly Gly Leu Val Leu Gln Asn Tyr Arg Leu Leu Asp Ala Thr Leu Tyr
65                  70                  75                  80

Val Thr Leu Glu Pro Cys Val Met Cys Ala Gly Ala Met Val His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Asp Val Thr Glu Gly Val Leu Arg Asp Glu Cys Ala Thr Leu Leu
    130                 135                 140

Ser Asp Phe Phe Arg Met Arg Arg Gln Glu Ile Lys Ala Leu Lys Lys
145                 150                 155                 160

Ser Ala Asn Gln


<210> SEQ ID NO 12
<211> LENGTH: 169
<212> TYPE: PRT
<213> ORGANISM: Kosakonia pseudosacchari

<400> SEQUENCE: 12

Met Ser Ile Pro Glu Leu Asn His Asp Val Trp Met Arg His Ala Leu
```

-continued

```
1               5                   10                  15

Thr Leu Ala Lys Arg Ala Arg Glu Glu Gly Glu Val Pro Val Gly Ala
            20                  25                  30

Val Leu Val His Asn Gly Gln Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Ile Asp Thr Thr Leu
65                  70                  75                  80

Tyr Val Thr Leu Glu Pro Cys Val Met Cys Ala Gly Ala Met Val His
                85                  90                  95

Ser Arg Ile Gly Gln Leu Val Phe Gly Ala Arg Asp Ala Lys Thr Gly
            100                 105                 110

Ala Ala Gly Ser Leu Ile Asp Val Leu His His Pro Gly Met Asn His
        115                 120                 125

Arg Val Glu Ile Thr Glu Gly Val Leu Arg Asp Glu Cys Ala Ala Met
    130                 135                 140

Leu Ser Asp Phe Phe Arg Gln Arg Arg Leu Glu Lys Lys Ala Leu Lys
145                 150                 155                 160

Lys Pro Thr Gly Asp Pro Thr Ala Phe
                165


<210> SEQ ID NO 13
<211> LENGTH: 163
<212> TYPE: PRT
<213> ORGANISM: Pluralibacter gergoviae

<400> SEQUENCE: 13

Met Ser Asp Thr Glu Gln His Glu Tyr Trp Met Arg His Ala Leu Thr
1               5                   10                  15

Leu Ala Arg His Ala Trp Asp Glu Gly Glu Val Pro Val Gly Ala Val
            20                  25                  30

Leu Val His Glu Gly Asn Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Ala Val Leu Gln Asn Tyr Arg Leu Ile Asn Ala Thr Leu Tyr
65                  70                  75                  80

Val Thr Leu Glu Pro Cys Val Met Cys Ala Gly Ala Met Val His Ser
                85                  90                  95

Arg Ile Ala Arg Leu Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Val Leu Gly Ala Glu Cys Ala Ser Leu Leu
    130                 135                 140

Ser Asp Phe Phe Arg Gln Arg Arg Glu Gln Lys Lys Ala Leu Lys Arg
145                 150                 155                 160

Gly Cys Cys


<210> SEQ ID NO 14
<211> LENGTH: 180
<212> TYPE: PRT
<213> ORGANISM: Klebsiella pneumoniae

<400> SEQUENCE: 14
```

-continued

```
Met Arg Pro Ala Phe Ser Ala Gly Val Ala Ala Val Ser Asp Leu Glu
1               5                   10                  15

Leu Asn Asp Glu Tyr Trp Met Arg His Ala Leu Thr Leu Ala Lys Arg
            20                  25                  30

Ala Arg Glu Glu Gly Glu Val Pro Val Gly Ala Val Leu Val His Asn
        35                  40                  45

Asn Gln Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Leu Gln Asn Tyr Arg Leu Ile Asp Ala Thr Leu Tyr Val Thr Leu Glu
                85                  90                  95

Pro Cys Val Met Cys Ala Gly Ala Met Val His Ser Arg Ile Ala Arg
            100                 105                 110

Leu Val Phe Gly Ala Arg Asp Ala Lys Thr Gly Ala Ala Gly Ser Leu
        115                 120                 125

Met Asp Val Leu His His Pro Gly Met Asn His Arg Val Glu Ile Ser
    130                 135                 140

Glu Gly Val Leu Ala Glu Ser Cys Ser Ala Met Leu Ser Asp Phe Phe
145                 150                 155                 160

Arg Trp Arg Arg Glu Glu Lys Lys Ala Leu Lys Lys Ala Arg Glu Gln
                165                 170                 175

Thr Gly Glu Ser
            180


<210> SEQ ID NO 15
<211> LENGTH: 180
<212> TYPE: PRT
<213> ORGANISM: Superficieibacter electus

<400> SEQUENCE: 15

Met Tyr Asn Ala Pro Arg Phe Leu Ala Gly Val Pro Ala Leu Ser Asn
1               5                   10                  15

His Glu Leu Asn His Glu His Trp Met Arg His Ala Leu Thr Leu Ala
            20                  25                  30

Gln Arg Ala Trp Asp Glu Gly Glu Val Pro Val Gly Ala Val Leu Val
        35                  40                  45

His Asp Asn Arg Val Ile Gly Glu Gly Trp Asn Arg Pro Ile Gly Arg
    50                  55                  60

His Asp Pro Thr Ala His Ala Glu Ile Met Ala Leu Arg Gln Gly Gly
65                  70                  75                  80

Leu Val Leu Gln Asn Tyr Arg Leu Ile Asp Thr Thr Leu Tyr Val Thr
                85                  90                  95

Leu Glu Pro Cys Val Met Cys Ala Gly Ala Met Val His Ser Arg Ile
            100                 105                 110

Gly Gln Leu Val Phe Gly Ala Arg Asp Ala Lys Thr Gly Ala Ala Gly
        115                 120                 125

Ser Leu Ile Asp Val Leu His His Pro Gly Met Asn His Arg Val Glu
    130                 135                 140

Phe Thr Glu Gly Val Leu Gly Glu Glu Cys Ala Ala Leu Leu Ser Asp
145                 150                 155                 160

Phe Phe Arg His Arg Arg Gln Val Lys Lys Ala Leu Arg Gln Ala Glu
                165                 170                 175

Lys Ser Gln Asp
```

180

<210> SEQ ID NO 16
<211> LENGTH: 179
<212> TYPE: PRT
<213> ORGANISM: Cronobacter malonaticus

<400> SEQUENCE: 16

Met Leu Pro Glu Lys Leu Val Ser Gln Thr Glu Leu Thr His Glu Tyr
1               5                   10                  15

Trp Met Arg His Ala Leu Thr Leu Ala Gln Arg Ala Trp Asp Glu Gly
            20                  25                  30

Glu Val Pro Val Gly Ala Val Leu Val His Asn Asn Gln Val Ile Gly
        35                  40                  45

Glu Gly Trp Asn Arg Pro Ile Gly Arg His Asp Pro Thr Ala His Ala
    50                  55                  60

Glu Ile Met Ala Leu Arg Gln Gly Gly Leu Val Leu Gln Asn Tyr Arg
65                  70                  75                  80

Leu Leu Asp Thr Thr Leu Tyr Val Thr Leu Glu Pro Cys Val Met Cys
                85                  90                  95

Ala Gly Ala Met Val His Gly Arg Ile Gly Thr Leu Val Phe Gly Ala
            100                 105                 110

Arg Asp Ala Lys Thr Gly Ala Val Gly Ser Leu Met Asp Ile Thr Gly
        115                 120                 125

His Pro Gly Met Asn His Gln Val Gln Val Ile Glu Gly Ile Leu Ala
    130                 135                 140

Thr Glu Cys Ser Ala Met Leu Ser Ala Phe Phe Arg Gln Arg Arg Leu
145                 150                 155                 160

Glu Lys Lys Ala Leu Lys Glu Ala Thr Lys Arg Ala Thr Gly Ser Asp
                165                 170                 175

Pro Ala Ala

<210> SEQ ID NO 17
<211> LENGTH: 150
<212> TYPE: DNA
<213> ORGANISM: Zea mays

<400> SEQUENCE: 17
cccacggccc aatacgaagc accgcgacga agcccaaaca gcagtccgta ggtggagcaa 60
agcgctgggt aatacgcaaa cgttttgtcc caccttgact aatcacaaga gtggagcgta 120
ccttataaac cgagccgcaa gcaccgaatt 150

<210> SEQ ID NO 18
<211> LENGTH: 173
<212> TYPE: DNA
<213> ORGANISM: Zea mays

<400> SEQUENCE: 18
tctgcttttt cgcatgatat ctgggccgca ccaaagaatc cagcccacgc ggcgtggcgc 60
cgtcgttacg gcttgcgggg gaaggaaacg agggacgaac cgagatttag caccagaccg 120
gccagcgagc attgcagaca ccggcttata agttcagctg cgactaccac tcc 173

<210> SEQ ID NO 19
<211> LENGTH: 163
<212> TYPE: DNA
<213> ORGANISM: Zea mays

-continued

<400> SEQUENCE: 19
cgtgatgtat gggccgcgcc taagcatcca gcccacgcgg gcgtgcgcgt cgtcgctacg 60
gcttgcgggg gaagggatca agggacgaac cgagaactag taccagaccg gccagcgagc 120
attgcagaca ccggcttata agttcagctg cgaccaccgc tcc 163

<210> SEQ ID NO 20
<211> LENGTH: 154
<212> TYPE: DNA
<213> ORGANISM: Zea mays

<400> SEQUENCE: 20
tccatggccc attataaagc accgccacaa agcccaaata gcagttcgtc ggtggagcaa 60
gcatcgcgct aggcaacagg caaacagttt gtcccacctc gtccagtcac aaaataaaag 120
cacgagttat aaaccaaacc ggaagcaccg catc 154

<210> SEQ ID NO 21
<211> LENGTH: 166
<212> TYPE: DNA
<213> ORGANISM: Zea mays

<400> SEQUENCE: 21
ccctgttccg ctttgctagc ttgcgccctg actgtccagc ccacgcgctt cggtccgatt 60
cacatgctag gctggtgcaa gcgagccgag actttttttt agaaccacct tgctcagcaa 120
accttaggaa caccggctta taagtcgaag cgaagcgctg tgcact 166

<210> SEQ ID NO 22
<211> LENGTH: 156
<212> TYPE: DNA
<213> ORGANISM: Zea mays

<400> SEQUENCE: 22
tcaatggccc attatataaa gcaccgccac aaagcccaaa taccagttcg tcggtggagc 60
aagtaacgcg ctaggcaaca ggcaaacagt ttgtcccacc tcgtccagtc acaaaggcaa 120
agcgtgactt ataagccaga gcggaagaac catacc 156

<210> SEQ ID NO 23
<211> LENGTH: 77
<212> TYPE: RNA
<213> ORGANISM: Artificial
<220> FEATURE:
<223> OTHER INFORMATION: sgRNA 1

<400> SEQUENCE: 23
guuuuagagc uagaaauagc aaguuaaaau aaggcuaguc cguuaucaac uugaaaaagu 60
ggcaccgagu cggugcu 77

<210> SEQ ID NO 24
<211> LENGTH: 81
<212> TYPE: RNA
<213> ORGANISM: Artificial
<220> FEATURE:
<223> OTHER INFORMATION: sgRNA 2

<400> SEQUENCE: 24
guuuuagagc uggaaacagc gaguuaaaau aaggcuuugu ccguacacaa cuuguaaaag 60
gggcacccga uucgggugca u 81

-continued

```
<210> SEQ ID NO 25
<211> LENGTH: 74
<212> TYPE: RNA
<213> ORGANISM: Artificial
<220> FEATURE:
<223> OTHER INFORMATION: sgRNA 3

<400> SEQUENCE: 25

guuuuagagc uggaaacagc aaguuaaaau aaggcuuugu ccguuuccaa cauuuguggc      60

gcugucucgg cgcu                                                        74


<210> SEQ ID NO 26
<211> LENGTH: 78
<212> TYPE: RNA
<213> ORGANISM: Artificial
<220> FEATURE:
<223> OTHER INFORMATION: sgRNA 4

<400> SEQUENCE: 26

guuuuagagc uagaaauagc gaguuaaaau aaggcuaguc cguaaucaac uugaaaaagu      60

gagcaccgag ucggugcu                                                    78
```